(12) United States Patent
Lee et al.

(10) Patent No.: US 12,176,101 B2
(45) Date of Patent: Dec. 24, 2024

(54) WIRELESS SERVICE TECHNOLOGY FOR PATIENT SUPPORT APPARATUSES

(71) Applicant: Stryker Corporation, Kalamazoo, MI (US)

(72) Inventors: Frank J. Lee, Kalamazoo, MI (US); Jeremy L. Dunn, Portage, MI (US); Krishna Sandeep Bhimavarapu, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 687 days.

(21) Appl. No.: 17/241,842

(22) Filed: Apr. 27, 2021

(65) Prior Publication Data
US 2022/0344040 A1    Oct. 27, 2022

(51) Int. Cl.
| | |
|---|---|
| *G16H 40/63* | (2018.01) |
| *G06F 8/65* | (2018.01) |
| *G06K 19/06* | (2006.01) |
| *H04W 12/06* | (2021.01) |
| *H04W 76/11* | (2018.01) |
| *H04W 76/15* | (2018.01) |

(52) U.S. Cl.
CPC .............. *G16H 40/63* (2018.01); *G06F 8/65* (2013.01); *G06K 19/06037* (2013.01); *H04W 12/06* (2013.01); *H04W 76/11* (2018.02); *H04W 76/15* (2018.02)

(58) Field of Classification Search
CPC ...... G16H 40/63; H04W 76/15; H04W 76/11; H04W 12/06; G06F 8/65; G06K 19/06037
See application file for complete search history.

(56) References Cited

U.S. PATENT DOCUMENTS

| | | | |
|---|---|---|---|
| 7,154,397 B2 | 12/2006 | Zerhusen et al. | |
| 7,242,306 B2 | 7/2007 | Wildman et al. | |
| 7,248,933 B2 | 7/2007 | Wildman | |
| 7,992,773 B1 | 8/2011 | Rothschild | |
| 8,334,779 B2 | 12/2012 | Zerhusen et al. | |
| 8,424,752 B2 | 4/2013 | Rothschild | |

(Continued)

OTHER PUBLICATIONS

Stryker PROfess Navigation Pattern Recognition Optics for Endoscopic Sinus Surgery.

(Continued)

*Primary Examiner* — Oleg Korsak
(74) *Attorney, Agent, or Firm* — Warner Norcross + Judd LLP

(57) ABSTRACT

A patient support apparatus and a portable service tool are adapted to communicate with each other in order to allow a user of the service tool to wirelessly update software executed by the patient support apparatus. In some embodiments, the patient support apparatus displays a coded message that encodes network credentials (e.g. SSID, password, etc.) and the software tool is adapted to capture an image of the coded message, decode the message, and then set up a wireless network having the decoded network credentials. The patient support apparatus then automatically joins the network and receives one or more wireless software updates. The service tool may alternatively or additionally connect to a healthcare facility network and upload software to a server thereon, which then downloads the software to the patient support apparatus over the healthcare facility computer network.

8 Claims, 12 Drawing Sheets

(56) References Cited

U.S. PATENT DOCUMENTS

| | | |
|---|---|---|
| 8,651,369 B2 | 2/2014 | Rothschild |
| 8,844,820 B2 | 9/2014 | Tallent et al. |
| 8,936,190 B2 | 1/2015 | Rothschild |
| 8,985,437 B2 | 3/2015 | Burkhart et al. |
| 9,286,560 B2 | 3/2016 | Burkhart et al. |
| 9,569,591 B2 | 2/2017 | Vanderpohl, III |
| 10,032,057 B2 | 7/2018 | Burkhart et al. |
| 10,070,789 B2 | 9/2018 | Collins, Jr. et al. |
| 10,235,762 B1 | 3/2019 | Wylie et al. |
| 10,456,309 B2 | 10/2019 | Constant et al. |
| 10,591,576 B1 | 3/2020 | Tang et al. |
| 10,685,742 B2 | 6/2020 | Walker |
| 10,708,745 B2 | 7/2020 | Gravelle et al. |
| 10,709,624 B2 * | 7/2020 | Bhimavarapu ........ A61G 7/018 |
| 10,893,027 B2 | 1/2021 | Khassanov et al. |
| 10,955,520 B2 | 3/2021 | Chua et al. |
| 2015/0231006 A1 * | 8/2015 | Bhimavarapu ........ A61G 7/018 5/621 |
| 2016/0259609 A1 * | 9/2016 | Tomita .................. H04W 48/20 |
| 2020/0082937 A1 | 3/2020 | Bodurka et al. |
| 2020/0203007 A1 | 6/2020 | Durlach et al. |
| 2021/0020307 A1 | 1/2021 | Bhimavarapu et al. |
| 2022/0095399 A1 | 3/2022 | Monson et al. |

OTHER PUBLICATIONS

Stryker ProCuity™ Bed Series Operations Manual [REF] 3009-009-001 Rev B.0 Aug. 2020.

* cited by examiner

WIRELESS SERVICE TECHNOLOGY FOR PATIENT SUPPORT APPARATUSES

BACKGROUND

The present disclosure relates to patient support apparatuses, such as beds, cots, stretchers, recliners, or the like, that include wireless communication abilities. More specifically, the present disclosure relates to a tool for wirelessly communicating with such patient support apparatuses in order to update software, download diagnostic data, and/or perform other service-related tasks with respect to the patient support apparatuses.

Existing hospital beds often include one or more microcontrollers and/or other types of controllers that execute software that occasionally needs to be updated. When such software updates are to be implemented, often they are performed via a wired connection, such as a USB cable coupled between the patient support apparatus and a laptop computer. When such software updates are performed wirelessly, efforts must be made to ensure that the technicians performing the updates know which patient support apparatus(es) they are wirelessly communicating with. In addition, it is important to ensure that unauthorized software updates are not allowed to be introduced to the patient support apparatuses and/or that unauthorized access to the patient support apparatuses is not granted.

SUMMARY

According to various embodiments, the present disclosure provides an improved tool for easily delivering software updates to one or more patient support apparatuses, for reading diagnostic information from one or more patient support apparatuses, and/or for performing one or more other service-related tasks with respect to one or more patient support apparatuses. In some embodiments, the tool includes enhanced security features that prevent unauthorized devices from joining a temporary wireless network used to deliver the software updates to the patient support apparatuses. The patient support apparatuses themselves are also configured, in at least some embodiments, to prevent themselves from being accessed by unauthorized wireless devices. These and other features of the present disclosure will become apparent to a person skilled in the art in light of the following written description and accompanying drawings.

A patient support apparatus according to a first embodiment of the present disclosure includes a support surface, a wireless network transceiver, a control, and a controller. The support surface is adapted to support a person thereon. The controller is adapted to communicate with the wireless network transceiver, the display, and the control. The controller is further adapted to display a coded image on the display in response to activation of the control. The coded image encodes a network identifier and the controller is adapted to use the wireless network transceiver to automatically connect to a temporary wireless network bearing the network identifier encoded within the coded image.

According to other aspects of the present disclosure, the coded image may include a Quick Response (QR) code.

In some embodiments, the wireless network transceiver is a WiFi transceiver and the network identifier includes a Service Set Identifier (SSID).

The controller, in some embodiments, is further adapted to display a different coded image in response to a subsequent activation of the control, wherein the different encoded image includes a different network identifier. The controller thereafter is adapted to use the wireless network transceiver to automatically connect to a different temporary wireless network that bears the identifier encoded with the different coded image.

In some embodiments, the network identifier is stored in a memory on board the patient support apparatus during the manufacturing process of the patient support apparatus.

In some embodiments, the controller is configured to randomly generate the network identifier.

The controller, in some embodiments, is configured to automatically connect to the wireless network only for a fixed amount of time after displaying the coded image on the display, and to not connect to the wireless network after the fixed amount of time expires.

In some embodiments, the controller is configured to only connect to the wireless network a single time such that, if the controller becomes disconnected from the wireless network, the controller is adapted to not automatically re-connect to the wireless network.

The controller, in some embodiments, is further configured to receive a software update from the wireless network.

In some embodiments, the coded image further encodes a password for the wireless network and the controller is adapted to use the password to connect to the wireless network.

The controller, in some embodiments, is further adapted to connect to a second wireless network different from the wireless network using the wireless network transceiver. In such embodiments, the controller is adapted to use a second network identifier different from the network identifier to connect to the second wireless network. The controller may be further configured to receive the software update from the second wireless network. The second wireless network may be a permanent healthcare facility network.

In some embodiments, the patient support apparatus further includes a Universal Serial Bus (USB) port adapted to receive a software update from a service tool coupled to the USB port via a USB cable.

According to another embodiment of the present disclosure, a patient support apparatus is provided that includes a support surface, a wireless network transceiver, a memory, and a controller. The support surface is adapted to support a person thereon. The memory contains a first network identifier and a second network identifier different from the first network identifier. The controller is adapted to use the wireless network transceiver to automatically connect to a first wireless network bearing the first network identifier, as well as to automatically connect to a second wireless network bearing the second network identifier.

According to other aspects of the present disclosure, the controller is further adapted to simultaneously connect to both the first wireless network and the second wireless network.

In some of the embodiments, one of the first and second wireless networks is a temporary wireless network used for communicating software updates, diagnostic information, etc. to/from the patient support apparatus, and the other of the first and second wireless networks is a permanent healthcare facility local area network.

The controller, in some embodiments, is further configured to receive a software update from both the first wireless network and the second wireless network.

The patient support apparatus, in some embodiments, further includes a display and a control, and the controller is adapted to display a coded image on the display in response to activation of the control, wherein the coded image encodes the second network identifier. In some such embodiments, the coded image includes a Quick Response (QR) code.

The wireless network transceiver, in some embodiments, is a WiFi transceiver. In such embodiments, the first network identifier may include a first Service Set Identifier (SSID), and the second network identifier may include a second SSID.

In some embodiments, the controller is further adapted to display a different coded image in response to a subsequent activation of the control. In such embodiments, the different encoded image includes a different network identifier and the controller is adapted to use the wireless network transceiver to automatically connect to a different wireless network identifier encoded with the different coded image.

In some embodiments, the controller is configured to automatically connect to the second wireless network only for a fixed amount of time after displaying the coded image on the display, and to not connect to the second wireless network after the fixed amount of time expires.

The controller, in some embodiments, is configured to only connect to the second wireless network a single time such that, if the controller becomes disconnected from the second wireless network, the controller is adapted to not automatically re-connect to the second wireless network.

The coded image, in some embodiments, further encodes a password for the second wireless network and the controller is adapted to use the password to connect to the second wireless network.

According to another embodiment of the present disclosure, a service tool is provided for wirelessly transmitting software updates to a patient support apparatus. The service tool includes a memory, a wireless network transceiver, a camera, and a controller. The memory includes a software application stored therein. The controller is in communication with the memory, the wireless network transceiver, and the camera. The controller is adapted to execute the software application and the software application is adapted to instruct the controller to perform the following: (a) decode a code contained within an image captured by the camera, wherein the image is taken of at least a portion of a patient support apparatus and the code encodes a network identifier; (b) advertise a wireless network using the network identifier and the wireless network transceiver; and (c) allow the patient support apparatus to join the wireless network.

According to other aspects of the disclosure, the software application is further configured to instruct the controller to download a software update to the patient support apparatus using the wireless transceiver after the patient support apparatus joins the wireless network.

In some embodiments of the service tool, the code is a Quick Response (QR) code.

In some embodiments of the service tool, the wireless network transceiver is a WiFi transceiver and the network identifier includes a Service Set Identifier (SSID).

The software application, in some embodiments, is further configured to instruct the controller to allow the patient support apparatus the join the wireless network only for fixed amount of time after decoding the code, and to not allow the patient support apparatus to join the wireless network after the fixed amount of time passes.

The software application may also, or alternatively, be further configured to instruct the controller to allow the patient support apparatus to join the wireless network only a single time, such that, if the patient support apparatus becomes disconnected from the wireless network, the controller is adapted to not allow the patient support apparatus to re-connect to the wireless network using the network identifier.

The code, in some embodiments, further encodes a password for the wireless network and the controller is adapted to allow the patient support apparatus to join the wireless network only if the patient support apparatus transmits the password to the controller via the wireless transceiver.

The service tool, in some embodiments, further comprises a Universal Serial Bus (USB) port, and the software application is further configured to instruct the controller to transmit a software update to the patient support apparatus via a USB cable coupled between the USB port and the patient support.

The software application, in some embodiments, is further configured to instruct the controller to use the wireless network transceiver to connect to a second wireless network. The second wireless network may include one or more servers hosted thereon that are in communication with the patient support apparatus.

In some embodiments, the software application is further configured to instruct the controller to transmit a software update to the patient support apparatus by transmitting the software update over the second wireless network.

The service tool, in some embodiments, further includes a display, and the software application is further configured to instruct the controller to display on the display a list of all patient support apparatuses in communication with the second wireless network.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
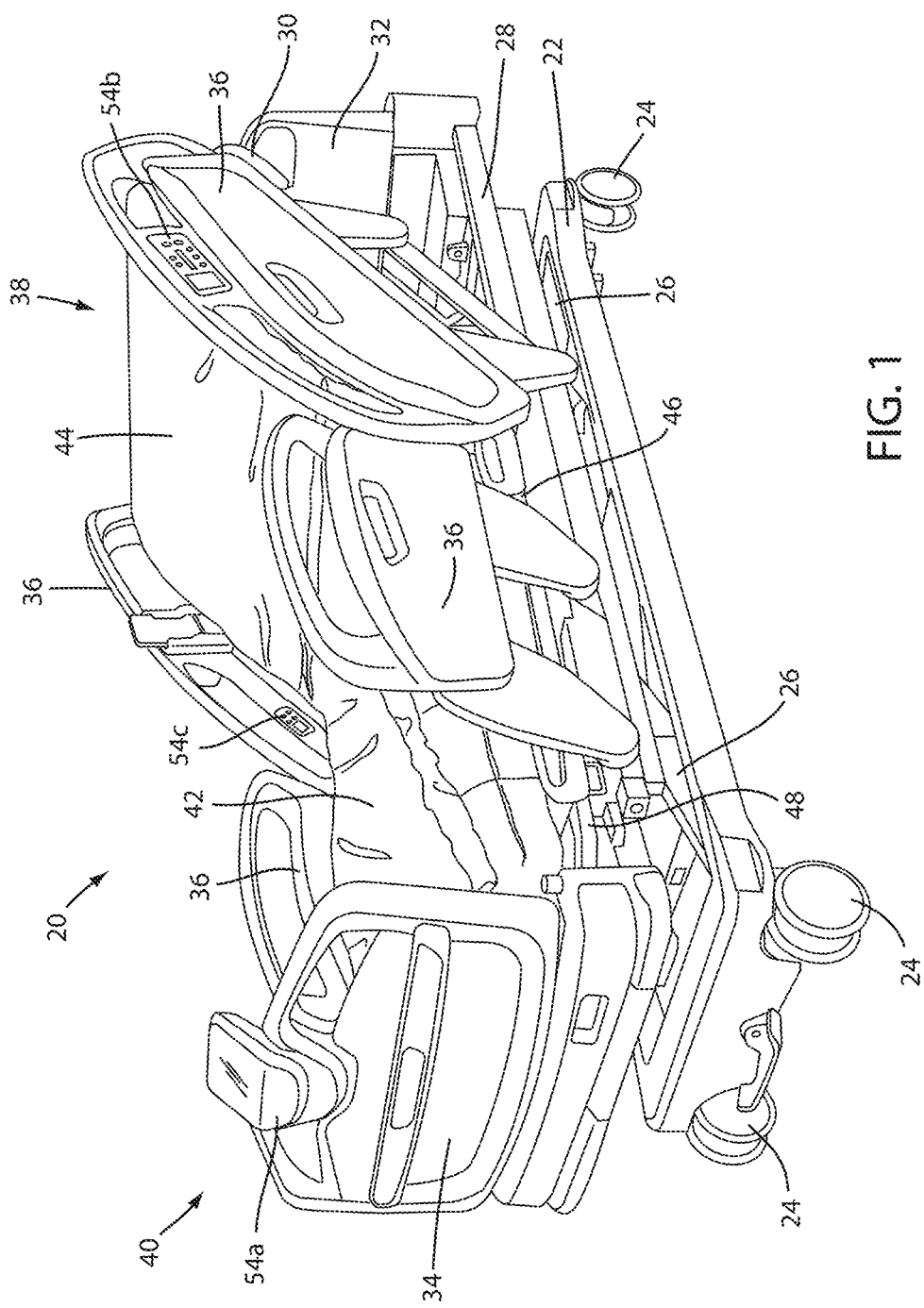
FIG. 1 is a perspective view of a patient support apparatus according to a first embodiment of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, or any other structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a headboard 32, a footboard 34 and a plurality of siderails 36. Siderails 36 are all shown in a raised position in FIG. 1 but are each individually movable to a lower position in which ingress into, and egress out of, patient support apparatus 20 is not obstructed by the lowered siderails 36.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 28 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Patient support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress 42, or other soft cushion, so that a person may lie and/or sit thereon. The top surface of the mattress 42 or other cushion forms a support surface for the occupant.

Support deck 30 is made of a plurality of sections, some of which are pivotable about generally horizontal pivot axes. In the embodiment shown in FIG. 1, support deck 30 includes at least a head section 44, a thigh section 46, and a foot section 48, all of which are positioned underneath mattress 42 and which generally form flat surfaces for supporting mattress 42. Head section 44, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

In some embodiments, patient support apparatus 20 may be modified from what is shown to include one or more components adapted to allow the user to extend the width of patient support deck 30, thereby allowing patient support apparatus 20 to accommodate patients of varying sizes. When so modified, the width of deck 30 may be adjusted sideways in any increments, for example between a first or minimum width, a second or intermediate width, and a third or expanded/maximum width.

As used herein, the term "longitudinal" refers to a direction parallel to an axis between the head end 38 and the foot end 40. The terms "transverse" or "lateral" refer to a direction perpendicular to the longitudinal direction and parallel to a surface on which the patient support apparatus 20 rests.

It will be understood by those skilled in the art that patient support apparatus 20 can be designed with other types of mechanical constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. In another embodiment, the mechanical construction of patient support apparatus 20 may be the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with still other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on still other forms different from what is disclosed in the aforementioned references.

Figure 2:
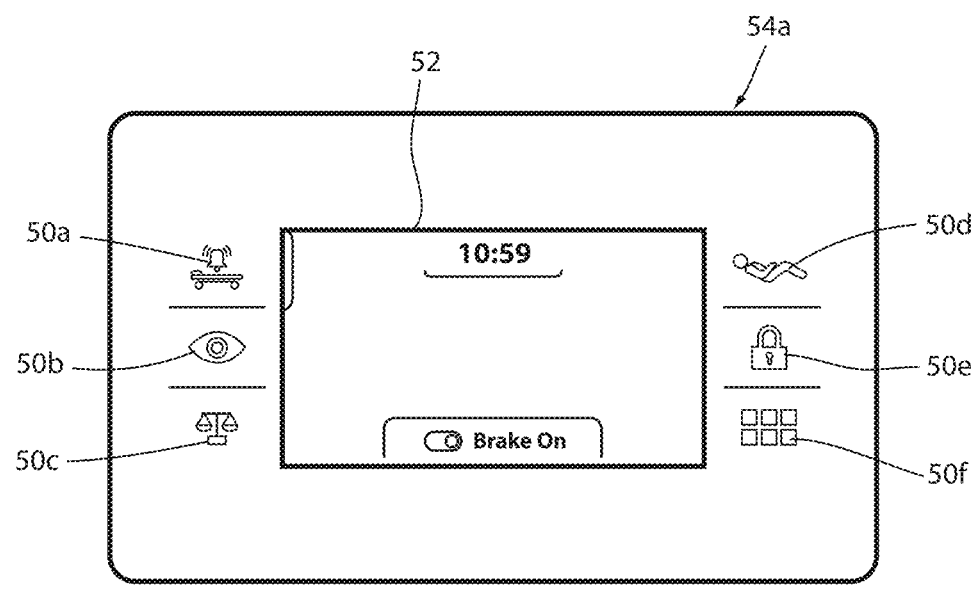
FIG. 2 is a plan view of an illustrative caregiver control panel of the patient support apparatus.

Patient support apparatus 20 further includes a plurality of control panels 54 that enable a user of patient support apparatus 20, such as a patient and/or an associated caregiver, to control one or more aspects of patient support apparatus 20. In the embodiment shown in FIG. 1, patient support apparatus 20 includes a footboard control panel 54a, a pair of outer siderail control panels 54b (only one of which is visible), and a pair of inner siderail control panels 54c (only one of which is visible). Footboard control panel 54*a* and outer siderail control panels 54*b* are intended to be used by caregivers, or other authorized personnel, while inner siderail control panels 54*c* are intended to be used by the patient associated with patient support apparatus 20. Each of the control panels 54 includes a plurality of controls 50 (see, e.g. FIGS. 2-3), although each control panel 54 does not necessarily include the same controls and/or functionality.

Among other functions, controls 50 of control panel 54*a* allow a user to control one or more of the following: change a height of support deck 30, raise or lower head section 44, activate and deactivate a brake for wheels 24, arm and disarm an exit detection system and, as will be explained in greater detail below, communicate with the particular IT infrastructure installed in the healthcare facility in which patient support apparatus 20 is positioned. One or both of the inner siderail control panels 54*c* also include at least one control that enables a patient to call a remotely located nurse (or other caregiver). In addition to the nurse call control, one or both of the inner siderail control panels 54*c* also include one or more controls for controlling one or more features of one or more room devices positioned within the same room as the patient support apparatus 20. As will be described in more detail below, such room devices include, but are not necessarily limited to, a television, a reading light, and a room light. With respect to the television, the features that may be controllable by one or more controls 50 on control panel 54*c* include, but are not limited to, the volume, the channel, the closed-captioning, and/or the power state of the television. With respect to the room and/or night lights, the features that may be controlled by one or more controls 50 on control panel 54*c* include the on/off state and/or the brightness level of these lights.

Control panel 54*a* includes a display 52 (FIG. 2) configured to display a plurality of different screens thereon. Surrounding display 52 are a plurality of navigation controls 50*a-f* that, when activated, cause the display 52 to display different screens on display 52. More specifically, when a user presses navigation control 50*a*, control panel 54*a* displays an exit detection control screen on display 52 that includes one or more icons that, when touched, control an onboard exit detection system. The exit detection system is as adapted to issue an alert when a patient exit from patient support apparatus 20. Such an exit detection system may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference.

When a user pressed navigation control 50*b* (FIG. 2), control panel 54 displays a monitoring control screen that includes a plurality of control icons that, when touched, control an onboard monitoring system built into patient support apparatus 20. Further details of one type of monitoring system that may be built into patient support apparatus 20 are disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, as well as commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses navigation control 50*c*, control panel 54*a* displays a scale control screen that includes a plurality of control icons that, when touched, control the scale system of patient support apparatus 20. Such a scale system may include any of the features and functions as, and/or may be constructed in any of the same manners as, the scale systems disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, and U.S. patent application Ser. No. 62/885,954 filed Aug. 13, 2019, by inventors Kurosh Nahavandi et al. and entitled PATIENT SUPPORT APPARATUS WITH EQUIPMENT WEIGHT LOG, the complete disclosures of both of which are incorporated herein by reference.

When a user presses navigation control 50*d*, control panel 54 displays a motion control screen that includes a plurality of control icons that, when touched, control the movement of various components of patient support apparatus 20, such as, but not limited to, the height of litter frame 28 and the pivoting of head section 44. In some embodiments, the motion control screen displayed on display 52 in response to pressing control 50*d* may be the same as, or similar to, the position control screen 216 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

When a user presses navigation control 50*e*, control panel 54*a* displays a motion lock control screen that includes a plurality of control icons that, when touched, control one or more motion lockout functions of patient support apparatus 20. Such a motion lockout screen may include any of the features and functions as, and/or may be constructed in any of the same manners as, the motion lockout features, functions, and constructions disclosed in commonly assigned U.S. patent application Ser. No. 16/721,133 filed Dec. 19, 2019, by inventors Kurosh Nahavandi et al. and entitled PATIENT SUPPORT APPARATUSES WITH MOTION CUSTOMIZATION, the complete disclosures of both of which are incorporated herein by reference.

When a user presses on navigation control 50*f*, control panel 54*a* displays a menu screen that includes a plurality of menu icons that, when touched, bring up one or more additional screens for controlling and/or viewing one or more other aspects of patient support apparatus 20. Such other aspects include, but are not limited to, diagnostic and/or service information for patient support apparatus 20, mattress control and/or status information, configuration settings, and other settings and/or information. One example of a suitable menu screen is the menu screen 100 disclosed in commonly assigned U.S. patent application Ser. No. 62/885,953 filed Aug. 13, 2019, by inventors Kurosh Nahavandi et al. and entitled PATIENT SUPPORT APPARATUS WITH TOUCHSCREEN, the complete disclosure of which is incorporated herein by reference.

For all of the navigation controls 50*a-f* (FIG. 2), screens other than the ones specifically mentioned above may be displayed on display 52 in other embodiments of patient support apparatus 20 in response to a user pressing these controls. Thus, it will be understood that the specific screens mentioned above are merely representative of the types of screens that are displayable on display 52 in response to a user pressing on one or more of navigation controls 50*a-f*. It will also be understood that, although navigation controls 50*a-f* have all been illustrated in the accompanying drawings as dedicated controls that are positioned adjacent display 52, any one or more of these controls 50*a-f* could alternatively, or additionally, be touchscreen controls that are displayed at one or more locations on display 52. Still further, although controls 50*a-f* have been shown herein as buttons, it will be understood that any of controls 50*a-f* could also, or alternatively, be switches, dials, or other types of non-button controls.

It will also be understood that, in some embodiments, any one or more of control panels 54*a-c* may include any one or more of the controls 50*g-t* disclosed in commonly assigned U.S. patent application Ser. No. 63/131,508 filed Dec. 29, 2020 by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

Figure 3:
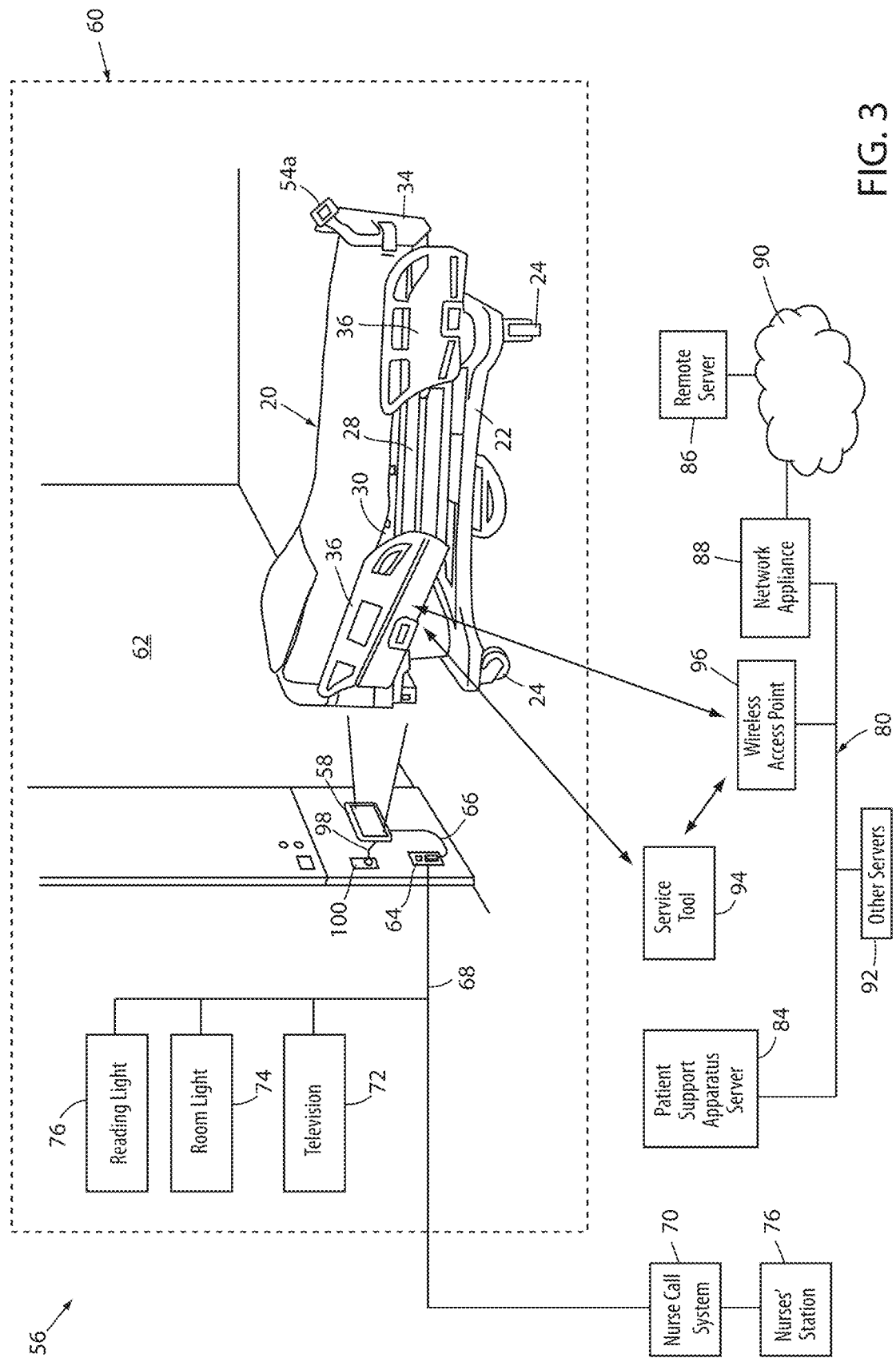
FIG. 3 is a diagram of the patient support apparatus shown coupled to the IT infrastructure of a healthcare facility in a common manner.

FIG. 3 illustrates patient support apparatus 20 positioned in a typical room 60 of a conventional healthcare facility 56. As shown in FIG. 3, room 60 includes a headwall 62 into which a conventional communications outlet 64 is physically integrated. Communications outlet 64 is adapted to receive a nurse call cable 66 that physically connects at its other end either to patient support apparatus 20 (not shown) or to a wireless headwall unit 58 (shown in FIG. 4). In many healthcare facilities, communication outlet 64 includes a 37-pin connector, although other types of connectors are often found in certain healthcare facilities. As will be discussed in greater detail below, headwall unit 58 and nurse call cable 66 allow patient support apparatus 20 to communicate with a nurse call system, and one or more room devices positioned within room 60.

Communication outlet 64 is electrically coupled to one or more cables, wires, or other conductors 68 that electrically couple the communication outlet 64 to a nurse call system 70 and one or more room devices, such as a television 72, a room light 74, and/or a reading light 76. Conductors 68 are typically located behind headwall 62 and not visible. In some healthcare facilities, conductors 68 may first couple to a room interface circuit board that includes one or more conductors 68 for electrically coupling the room interface circuit board to room devices 72, 74, 76 and/or nurse call system 70. Still other communicative arrangements for coupling communication outlet 64 to nurse call system 70 and/or one or more room devices 72, 74, 76 are possible.

Room devices 72, 74, 76 are conventional room devices that are typically present in a conventional hospital room. In most cases, the particular brand and model of the television 72 and/or lights 74, 76 will vary from healthcare facility to healthcare facility, and may vary from room to room within the same healthcare facility. The different models and/or brands of televisions 72, room lights 74, and/or reading lights 76 are often controlled in different manners. For example, the signals that are input into a first brand of television in order to change a channel may require a first voltage level, while the signals that are input into a second brand of television in order to change the channel may require a second voltage level. Still further, apart from differences in voltage levels, the sequence of bits and/or other information that is sent to a television to change the channel, for example, may vary from brand to brand, or from model to model. Still other aspects of the control of the television 72 and/or lights 74, 76 may vary from brand to brand and/or from model to model. Thus, in order for a patient to properly control the television 72 and/or lights 74, 76 using one of the patient control panels 54*c*, patient support apparatus 20 or headwall unit 58 need to be properly configured to match the particular television 72 and/or lights 74, 76 that are positioned in the same room as the patient support apparatus 20. In the systems described herein, headwall units 58 are configured to match the associated televisions 72 and/or lights 74, 76, as well as the associated nurse call system 70.

Nurse call cable 66 (FIG. 3) enables patient support apparatus 20 to communicate with nurse call system 70 and/or room devices 72, 74, 76. A patient supported on patient support apparatus 20 who activates a nurse call control on patient support apparatus 20 causes a signal to be wirelessly sent from patient support apparatus 20 to headwall unit 58, which in turn conveys the signal via nurse call cable 66 to the nurse call system 70, which forwards the signal to a one or more remotely located nurses (e.g. nurses at one or more nurses' stations 78). If the patient activates one or more room device controls 50 on control panel 54*c*, one or more wireless signals are conveyed to headwall unit 58, which in turn sends appropriate signals via nurse call cable 66 to communication outlet 64 and the room devices 72, 74, 76 that change one or more features of these devices (e.g. the volume, channel, on/off state, etc.).

As is also shown in FIG. 3, patient support apparatus 20 is further configured to communicate with a local area network 80 of the healthcare facility. In this embodiment, patient support apparatus 20 includes a wireless network transceiver 82 (FIG. 4) that communicates wirelessly with local area network 80. Network transceiver 82 is, in at least some embodiments, a WiFi transceiver (e.g. IEEE 802.11) that wirelessly communicates with one or more conventional wireless access points 96 of local area network 80. In other embodiments, network transceiver 82 may be a wireless transceiver that uses conventional 5G technology to communicate with LAN 80, a server hosted thereon, and/or another device. In some embodiments, network transceiver 82 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

In some embodiments, network transceiver 82 is a wired transceiver that is adapted to allow patient support apparatus 20 to communicate with network 80 via a wired connection, such as an Ethernet cable that plugs into an Ethernet port (e.g. an RJ-45 style port, an 8P8C port, etc.) built into patient support apparatus 20. In still other embodiments, patient support apparatus 20 includes both a wired transceiver 82 for communicating with network 80 via a wired connection and a wireless transceiver 82 for wirelessly communicating with network 80.

Patient support apparatus 20 is configured to communicate with one or more servers on local area network 80 of the healthcare facility. One such server is a patient support apparatus server 84. Patient support apparatus server 84 is adapted, in at least one embodiment, to receive status information from patient support apparatuses 20 positioned within the healthcare facility and distribute this status information to caregivers, other servers, and/or other software applications. In some embodiments, patient support apparatus server 84 is configured to communicate at least some of the status data received from patient support apparatuses 20 to a remote server 86 that is positioned geographically remotely from the healthcare facility. Such communication may take place via a network appliance 88, such as, but not limited to, a router and/or a gateway, that is coupled to the Internet 90. The remote server 86, in turn, is also coupled to the Internet 90, and patient support apparatus server 84 is provided with the URL and/or other information necessary to communicate with remote server 86 via the Internet connection between network 80 and server 86.

Local area network 80 is also configured to allow one or more service tools 94 to access the local area network 80 via wireless access points 96. Such service tools 94, as will be discussed in greater detail below, are adapted to provide software updates to one or more patient support apparatuses 20 positioned within healthcare facility 56, to read diagnostic information from one or more patient support apparatuses 20 positioned within the healthcare facility 56, to configure one or more settings onboard the patient support apparatuses 20, and/or to carry out any one or more other tasks that involve communication between the patient support apparatuses 20 and the service tools 94. Service tools 94 may take on a variety of different forms. In many embodiments, a service tool 94 includes a conventional electronic device that is configured to execute a specialized software application. For example, in many embodiments, service tool 94 is a small, relatively portable, hand-held device, such as a smart phone, a tablet computer, a portable laptop, or another type of electronic device that include WiFi capability and that can execute one or more software applications designed to carry out the service tool functions described herein.

It will be understood that the architecture and content of local area network 80 will vary from healthcare facility to healthcare facility, and that the example shown in FIG. 3 is merely one example of the type of network a healthcare facility may be employ. Typically, additional servers 92 will be hosted on network 80 and one or more of them may be adapted to communicate with patient support apparatus server 84. For example, an electronic health record server will typically be present in any healthcare facility, and in some embodiments discussed herein, it will be in communication with patient support apparatus server 84 in order to receive patient data that is to be recorded in a patient's health record (e.g. weight readings taken from the scales built into patient support apparatuses 20; therapies provided to patients using a powered mattress 42 onboard patient support apparatuses 20, data from a medical device that is determined to be associated with the patient assigned to patient support apparatus 20, etc.).

Headwall units 58 are adapted to wirelessly receive signals from patient support apparatus 20 and deliver the signals to communications outlet 64 in a manner that matches the way the signals would otherwise be delivered to communications outlet 64 if a conventional nurse call cable 66 were connected directly between patient support apparatus 20 and communications outlet 64. In other words, patient support apparatus 20 and headwall unit 58 cooperate to provide signals to communications outlet 64 in a manner that is transparent to communications outlet 64 such that outlet 64 cannot detect whether it is in communication with patient support apparatus 20 via a wired connection or it is in communication with patient support apparatus 20 via a wireless connection between patient support apparatus 20 and headwall unit 58 (the latter of which is in wired communication with outlet 64). In this manner, a healthcare facility can utilize the wireless communication abilities of one or more patient support apparatuses 20 without having to make any changes to their existing communication outlets 64.

In addition to sending signals received from patient support apparatus 20 to communications outlet 64, headwall units 58 are also adapted to forward signals received from communications outlet 64 to patient support apparatus 20. Headwall units 58 are therefore adapted to provide bidirectional communication between patient support apparatus 20 and communications outlet 64. In some embodiments, such communication includes communicating command signals from any of controls 50 and/or from any of service tools 94 to corresponding room devices 72, 74, and/or 76. Such communication also includes communicating audio signals between a person supported on patient support apparatus 20 and a caregiver positioned remotely from patient support apparatus 20. The audio signals received by headwall units 58 from a microphone on patient support apparatus 20 are forwarded to communications outlet 64, and the audio signals received from communications outlet 64 are forwarded to a speaker onboard patient support apparatus 20.

Nurse call cable 66, in some embodiments, includes a conventional 37 pin connector on each end, one of which is adapted to be inserted into outlet 64 and the other one of which is adapted to be inserted into headwall unit 58. Such 37 pin connections are one of the most common types of connectors found on existing headwalls of medical facilities for making connections to the nurse call system 70 and room devices 72, 74, and 76. Headwall unit 58 and nurse call cable 66 are therefore configured to mate with one of the most common type of communication outlets 64 used in medical facilities. Such 37 pin connectors, however, are not the only type of connectors, and it will be understood that headwall unit 58 can utilize different types of connectors that are adapted to electrically couple to different types of nurse call cables 66 and/or different types of communication outlets 64. One example of such an alternative communications outlet 64 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of communication outlets 64 and corresponding connectors may be utilized.

Headwall unit 58 (FIG. 4) also includes an electrical cord 98 having a plug positioned at a far end that is adapted to be inserted into a conventional electrical outlet 100. Electrical cord 98 enables headwall unit 58 to receive power from the mains electrical supply via outlet 100. It will be appreciated that, in some embodiments, headwall unit 58 is battery operated and cord 98 may be omitted. In still other embodiments, headwall unit 58 may be both battery operated and include cord 98 so that in the event of a power failure, battery power supplies power to headwall unit 58, and/or in the event of a battery failure, electrical power is received through outlet 100.

In addition to any of the structures and functions described herein, headwall units 58 may be configured to communicate location data to patient support apparatus 20 that enables patient support apparatus 20 and/or patient support apparatus server 84 to determine the location of patient support apparatus 20 within the healthcare facility. Such location determination may be carried out in any of the manners disclosed in commonly assigned U.S. Pat. No. 9,999,375 issued Jun. 19, 2018, to inventors Michael Hayes et al. and entitled LOCATION DETECTION SYSTEMS AND METHODS, the complete disclosure of which is incorporated herein by reference.

Headwall units 58 may also perform additional functions. In some embodiments, headwall units 58 may perform any of the functions performed by the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. In some embodiments, headwall units 58 may also, or alternatively, perform any of the same functions performed by the headwall interfaces 72 disclosed in commonly assigned U.S. patent application Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosure of which is also incorporated herein by reference. In still other embodiments, headwall units 58 may also, or alternatively, perform any of the same functions performed by the headwall units 66 disclosed in commonly assigned U.S. patent application Ser. No. 16/217,203 filed Dec. 12, 2018, by inventor Alexander Bodurka et al. and entitled SMART HOSPITAL HEADWALL SYSTEM, the complete disclosure of which is incorporated herein by reference.

In some embodiments, headwall units 58 may be constructed to include any or all of the functionality of the wireless headwall units disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference.

In some embodiments, headwall units 58 may also be constructed to include any or all of the functionality of the headwall units disclosed in commonly assigned U.S. patent application Ser. No. 63/26,937 filed May 19, 2020, by inventors Alexander Bodurka et al. and entitled PATIENT SUPPORT APPARATUSES WITH HEADWALL COMMUNICATION, the complete disclosure of which is also incorporated herein by reference.

Still further, in some embodiments, headwall units may be constructed to include any of the features and/or functions of the headwall units 144a disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference.

In some embodiments, patient support apparatuses 20 and headwall units 58 include one or more location transceivers and are adapted to automatically determine if a tagged medical device is positioned within a volume of space that includes patient support apparatus 20, thereby allowing an automatic association to be made between the tagged medical device and the patient assigned to that patient support apparatus 20. Further details of various manners in which patient support apparatus 20 and/or headwall unit 58 may be constructed and programmed in order to carry out this location determination and automatic patient association are disclosed in commonly assigned U.S. patent application Ser. No. 63/161,175 filed Mar. 15, 2021, by inventors Krishna Bhimavarapu et al. and entitled EXERCISE DEVICE AND PATIENT SUPPORT APPARATUS, the complete disclosure of which is incorporated herein by reference.

In some embodiments, patient support apparatus 20 and/or patient support apparatus server 84 may also include any or all of the functionality of the patient support apparatuses and/or patient support apparatus servers described in any of the aforementioned commonly assigned U.S. patents and/or patent applications.

Figure 4:
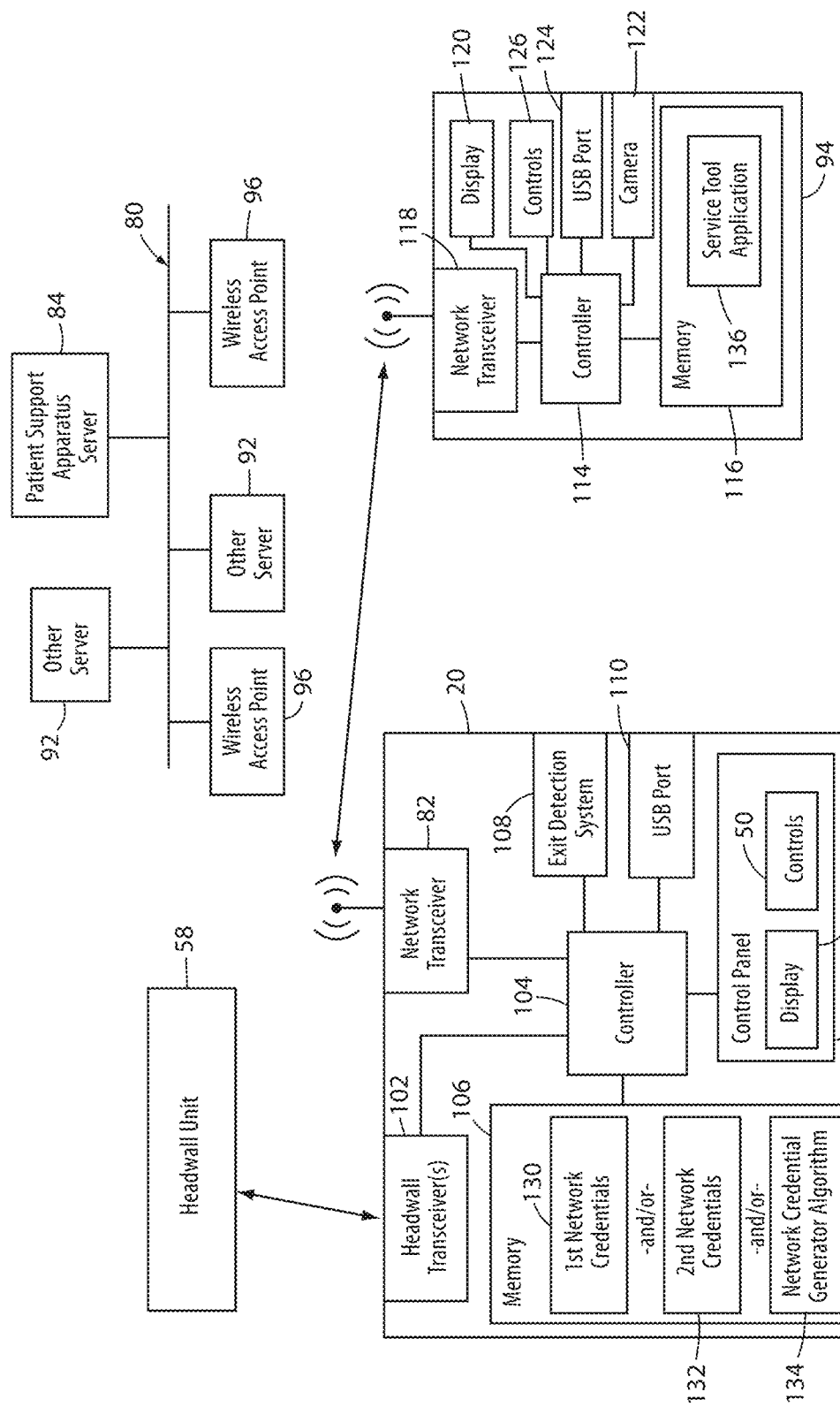
FIG. 4 is a block diagram a service tool and the patient support apparatus showing the service tool and patient support apparatus directly communicating with each other over a temporary wireless network.

FIG. 4 depicts in more detail the internal components of patient support apparatus 20 and service tool 94. It will be understood that these components are not necessarily a complete list of components onboard patient support apparatus 20 and/or service tool 94, and that patient support apparatus 20 and/or service tool 94 may therefore include additional components beyond those depicted in FIG. 4. Indeed, in some embodiments, patient support apparatus 20 may include any one or more of the components and/or features of any of the patient support apparatuses disclosed in any of the patent references incorporated herein by reference.

As shown in FIG. 4, patient support apparatus 20 includes network transceiver 82, a headwall transceiver 102, a controller 104, a memory 106, control panel 54a (as well additional control panels 54b, 54c which are not shown in FIG. 4), an exit detection system 108, and a Universal Serial Bus (USB) port 110. Each of these components are in communication with each other in one or more conventional manners, such as, but not limited to, one or more the following: a Controller Area Network (CAN); an I-Squared-C bus; a Local Interconnect Network (LIN) bus, Firewire; RS-232; RS-485; Universal Serial Bus (USB); Ethernet; a Serial Peripheral Interface (SPI) bus, and/or in other manners.

Service tool 94 includes a controller 114, a memory 116, a network transceiver 118, a display 120, a camera 122, a USB port 124, and one or more controls 126. Memory 116 includes a service tool software application 136 that is executed by controller 114 and, as was mentioned previously, service tool 94 may be a conventional smart phone, tablet computer, laptop computer, or other type of computer that is able to execute software application 136 and that includes the components shown in FIG. 4.

Controller 104 of patient support apparatus 20 and controller 114 of service tool 94 may take on a variety of different forms. In the illustrated embodiment (FIG. 4), controllers 104 and 114 are implemented as one or more conventional microcontrollers. However, controllers 104, 114 may be modified to use a variety of other types of circuits—either alone or in combination with one or more microcontrollers—such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controllers 104, 114 when carrying out the functions described herein, as well as the data necessary for carrying out these functions, are stored in corresponding memories 106, 116, respectively, that are accessible to that particular controller 104, 114.

Figure 11:
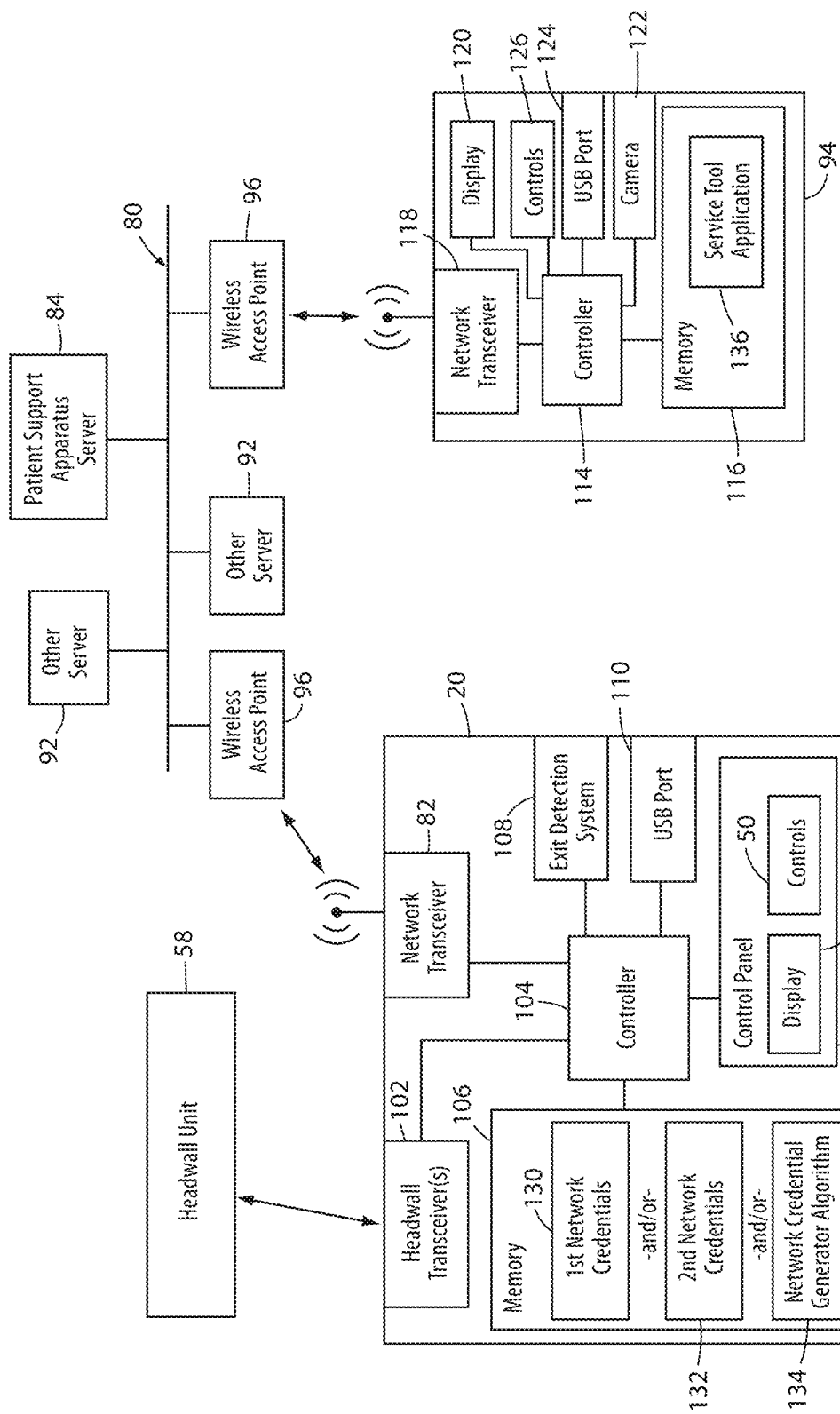
FIG. 11 is a block diagram the service tool and the patient support apparatus showing the service tool and patient support apparatus communicating with each other via a local area network of a healthcare facility.

Network transceivers 82 and 118 are, in at least some embodiments, WiFi transceivers (e.g. IEEE 802.11) that wirelessly communicate directly with each other (FIG. 4) or indirectly with each other via one or more conventional wireless access points 96 of local area network 80 (FIG. 11). In other embodiments, network transceivers 82, 118 may be wireless transceivers that uses conventional 5G technology to communicate directly with each other or indirectly with each other via LAN 80. In some embodiments, network transceivers 82, 118 may include any of the structures and/or functionality of the communication modules 56 disclosed in commonly assigned U.S. Pat. No. 10,500,401 issued to Michael Hayes and entitled NETWORK COMMUNICATION FOR PATIENT SUPPORT APPARATUSES, the complete disclosure of which is incorporated herein by reference. Still other types of wireless network transceivers may be utilized.

Exit detection system 108 of patient support apparatus 20 (FIG. 4) is adapted to issue an alert when a patient onboard patient support apparatus 20 exits therefrom. Exit detection system 108 may include any of the features and functions as, and/or may be constructed in any of the same manners as, the exit detection system disclosed in commonly assigned U.S. patent application 62/889,254 filed Aug. 20, 2019, by inventors Sujay Sukumaran et al. and entitled PERSON SUPPORT APPARATUS WITH ADJUSTABLE EXIT DETECTION ZONES, the complete disclosure of which is incorporated herein by reference. Alternatively, or additionally, exit detection system 108 may monitor the center of gravity of the patient and issue an alert, when armed, if the patient's center of gravity travels outside of a predefined zone or boundary, such as is explained in greater detail in U.S. Pat. No. 5,276,432 issued to Travis, the complete disclosure of which is incorporated herein by reference. Other types of exit detection systems may be included within patient support apparatus 20.

USB ports 110 and 124 are conventional USB ports that may take on a variety of different form factors (mini, micro, standard) and that may be configured to operate with any of the conventional USB standards (e.g. USB 1.0, USB 1.1, USB 2.0, USB 3.0, USB 3.1, USB 3.2, USB4, etc.). USB ports 110 are adapted to receive a conventional USB cable that is used to connect patient support apparatus 20 to service tool 94, thereby providing the user of service tool 94 the option of communicating with patient support apparatus 20 (via service tool 94) over a direct wired connection. As will be discussed in greater detail below, a user of service tool 94 can also, or alternatively, use service tool 94 to wirelessly communicate with patient support apparatus 20.

Headwall transceiver 102 of patient support apparatus 20 (FIG. 4) is adapted to wirelessly communicate with headwall unit 58. In some embodiments, headwall transceiver 102 includes both an RF (e.g. Bluetooth transceiver) and an infrared transceiver that are used to communication information to and from headwall unit 58, including information that enables the location of patient support apparatus 20 to be determined within healthcare facility 56. Headwall transceiver, in some embodiments, may include any of the structures, and/or perform any of the functions, of any of the IR transceivers 170 and RF transceivers 172 disclosed in commonly assigned U.S. patent application Ser. No. 63/26, 937 filed May 19, 2020, by inventors Alexander Bodurka et al. and entitled PATIENT SUPPORT APPARATUSES WITH HEADWALL COMMUNICATION, the complete disclosure of which is incorporated herein by reference. In some embodiments, headwall transceiver 102 may be omitted, in which case patient support apparatus 20 is adapted to communicate directly with communication outlet 64 via a nurse call cable 66 (and not utilize a headwall unit 58).

Memory 106 of patient support apparatus 20, in addition to including the data and instructions for carrying out the functions described herein, includes one or more of the data items shown in FIG. 4. These data items include a first set of network credentials 130, a second set of network credentials 132, and a network credential generator algorithm 134.

In some embodiments of patient support apparatus 20, memory 106 only includes first credentials 130 and algorithm 134. In other embodiments, memory 106 includes all three of these data items. In still other embodiments, patient support apparatus 20 only includes first credentials 130 and second credentials 132. Still other combinations are possible. Regardless of which specific data items are stored in memory 106, controller 104 uses these data items for setting up a temporary communication session with service tool 94, as will be discussed in greater detail below.

Display 120, camera 122, USB port 124, and controls 126 of service tool 94 (FIG. 4) may all be conventional structures found on commercially available smart phones, tablet computers, laptop computers, desktop computers, and/or other types of computers. Thus, display 120 may be a conventional LCD screen (either touch sensitive or not); camera 122 may be a conventional computer camera built into a phone, tablet, or computer; USB port 124 may be a conventional USB port that is typically found on most phones, tablets, and computers; and controls 126 may comprise one or more keys, switches, and/or touch sensitive sensors that are used to control the phone, tablet, or computer. Memory 116 of service tool 94 includes a service tool application 136 that is executed by controller 114 to carry out the service tool functions described herein. Memory 116 may also include additional software, firmware, and/or other data used for carrying out the functions described herein. Memory 116, as with memory 106, may be conventional flash memory, one or more hard drives, and/or any other type of non-volatile memory that is accessible by the respective controller 104, 114.

As was noted previously, service tool 94 is adapted to establish a temporary communication link with one or more patient support apparatuses 20 in at least two different manners: (a) a direct communication link that does not utilize the healthcare facility's network 80, and (b) an indirect communication link that uses the healthcare facility's network 80. This first manner is illustrated in FIG. 4 and the second manner is shown in FIG. 11.

Turning to the first manner of connecting service tool 94 to a patient support apparatus 20, service tool 94 is configured to advertise a wireless network (e.g. a WiFi network) that patient support apparatus 20 is programmed to automatically connect to. This WiFi network is separate from the network 80 of the healthcare facility (which may also include WiFi access points). In some embodiments, service tool 94 advertises a wireless network with the $1^{st}$ installed credentials 130 stored onboard patient support apparatus 20 (in memory 106). In other embodiments, service tool 94 advertises a wireless network with the second network credentials 132 stored onboard patient support apparatus 20. In still other embodiments, service tool 94 is configured to advertise a wireless network having credentials that are generated by patient support apparatus 20 using network credential generator algorithm 134. In all of these embodiments, the "credentials" refer to one or more of the following: the network's Service Set Identifier (SSID) (e.g. the network name), a password for the network, and/or other information necessary to be able to join the network. These different embodiments will be described in further detail below.

In the first embodiment, patient support apparatus 20 is configured to look for, and automatically connect to if it discovers, a network having the first credentials 130. These credentials 130 are installed during the manufacturing of the patient support apparatus. Thus, patient support apparatus 20 might be constructed such that credentials 130 correspond to a network named, for example, BedMfgNtwk with a password of Service3122. In such a case, after patient support apparatus 20 is powered on, controller 104 in combination with network transceiver 82 look for advertised networks bearing the name BedMfgNtwk and, if one is found, they attempt to connect to it using the password Service3122. If they are successful at connecting to the network, controller 104 is adapted to forward and receive data from the network.

When patient support apparatus 20 is constructed in the aforementioned manner, service tool application 136 is configured to instruct controller 114 of service tool 94 to advertise (using network transceiver 118) a network having the name BedMfgNtwk and the password Service3122 (i.e. a network having the same credentials as the factory-installed credentials 130 onboard patient support apparatus 20). Any patient support apparatuses 20 that are within range of network transceiver 118 will "hear" this advertisement and respond by joining the network. Once joined, service tool application 136 is adapted to allow a user to use service tool 94 to read diagnostic information from the joined patient support apparatuses 20; download new or updated software to the joined patient support apparatuses 20; view error events/logs, components, current software, available software, service counts, and/or serial numbers; and/or perform other communication tasks with the patient support apparatuses 20. One of these other tasks may be the installation of a new set of network credentials, such as, but not limited to, the network credentials necessary for patient support apparatus 20 to connect to the healthcare facility's local area network 80. If service tool 94 is used for this task, the user of service tool enters into service tool 94 the healthcare facility's network credentials, and controller 114 then forwards this information to patient support apparatus 20 via network transceiver 118 over the network having the credentials 130. Patient support apparatus 20 then stores this healthcare facility network credentials in memory 106 as second network credentials 132 and uses them to connect to local area network 80.

In some versions of this first embodiment, service tool 94 is not able to connect to the patient support apparatuses 20 if those patient support apparatuses 20 are already connected to the healthcare facility's local area network 80. This is because, in such versions, patient support apparatus 20 may include circuitry that only allows it to connect to a single WiFi network at a time. Thus, in such embodiments, if patient support apparatuses 20 are already connected to the healthcare facility's network 80 when service tool 94 is to be used, the user of service tool can utilize the healthcare facility's network 80 to connect to patient support apparatuses 20 (as discussed in more detail below with respect to FIG. 11). Alternatively, patient support apparatuses 20 may be constructed such that they are able to simultaneously connect to multiple WiFi networks (or other types of wireless networks) at the same time. When so constructed, the user of service tool 94 has the option of connecting service tool 94 directly to patient support apparatuses 20 via network transceiver 118 regardless of whether or not the patient support apparatuses 20 are already connected to the healthcare facility's network 80. In such embodiments, patient support apparatuses 20 may utilize first credentials 130 to connect to the healthcare facility network 80 and second credentials 132 to connect to service tool 94, or vice versa, and one of these sets of credentials may be preprogrammed during the manufacture of the patient support apparatus 20 (the one used to connect to service tool 94) and the other set of credentials may be programmable in the healthcare facility (the one used to connect to the healthcare facility network 80). In such embodiments, the service tool 94 may then be used to connect to the patient support apparatuses 20 and provide them with the healthcare facility's network 80 credentials.

Returning to the second embodiment discussed above, in which service tool 94 is configured to advertise a network with the second credentials 132, patient support apparatus 20 is configured to automatically connect to this network when it detects its presence. In this embodiment, patient support apparatus 20 may be configured to use first credentials 130 to connect to the healthcare facility network and second credentials 132 to connect to service tool 94. As was noted above, depending upon how patient support apparatus 20 is constructed, it may or may not be able to simultaneously connect to healthcare network 80 (using first credentials 130) and to the wireless network advertised by service tool 94 (using second credentials 132). If it is not able to simultaneously connect to both of these networks, and patient support apparatuses 20 are already connected to the healthcare facility network 80, then the user of service tool 94 will need to connect to patient support apparatuses 20 using the healthcare facility network 80, as discussed below with respect to FIG. 11. If it is able to simultaneously connect to both networks, then service tool 94 can utilize the second credentials 132 to connect to one or more patient support apparatuses 20, regardless of whether or not they are currently coupled to healthcare network 80 or not.

In either the first or second embodiments discussed above, patient support apparatus 20 may be configured to store one or more additional sets of network credentials (not shown) that are used for connecting to healthcare facility network 80 and/or for other purposes. Thus, patient support apparatuses 20 may be configured to automatically connect to one or more of multiple networks that have credentials that match at least one of the sets of credentials 130, 132 (and/or others) stored in memory 106.

Figure 5:
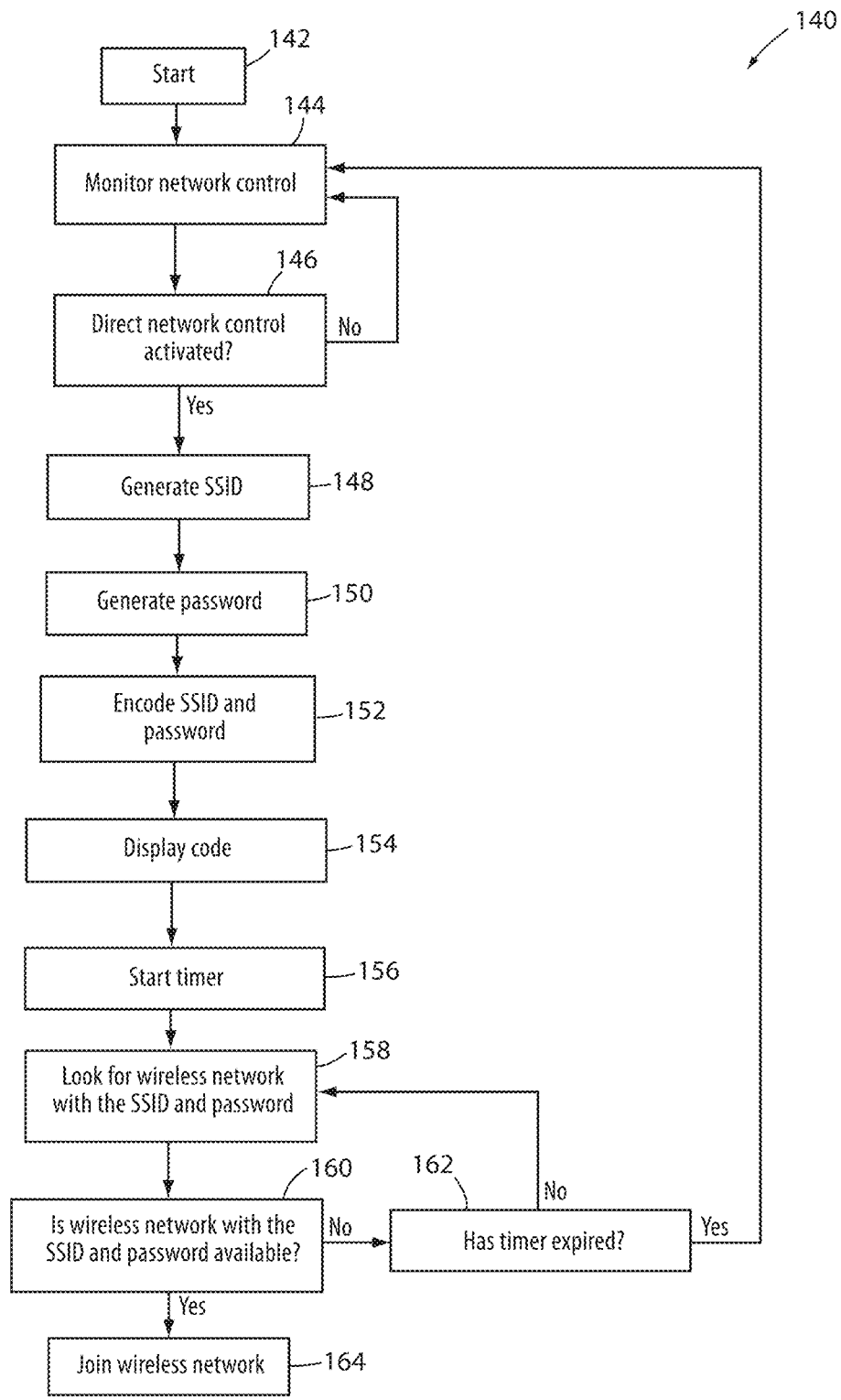
FIG. 5 is a flow diagram of an algorithm followed by some embodiments of the patient support apparatus.
Figure 6:
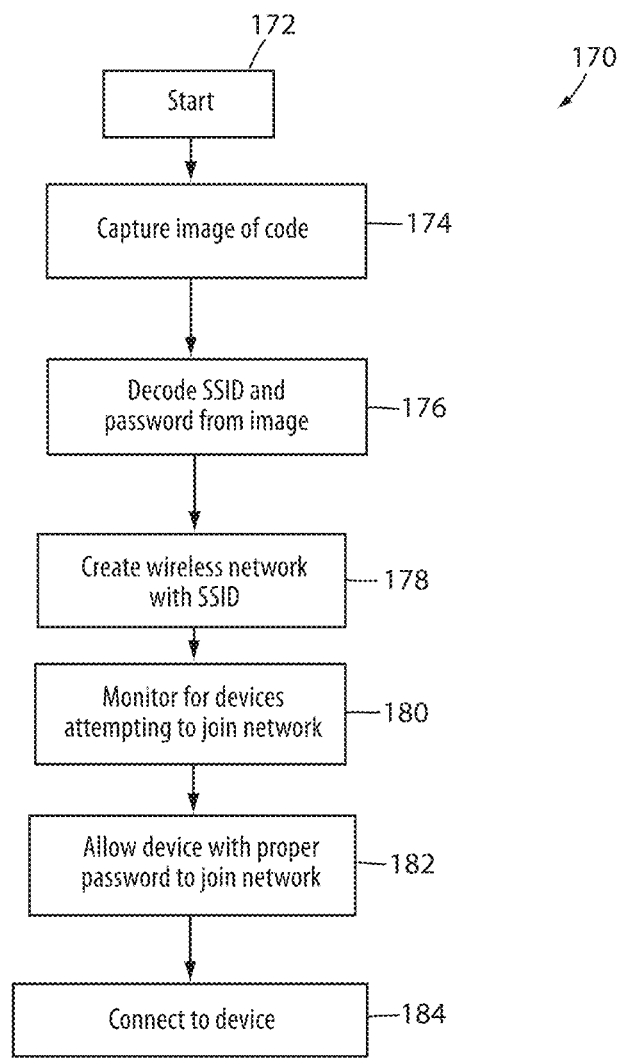
FIG. 6 is a flow diagram of an algorithm followed by some embodiments of the service tool.
Figure 7:
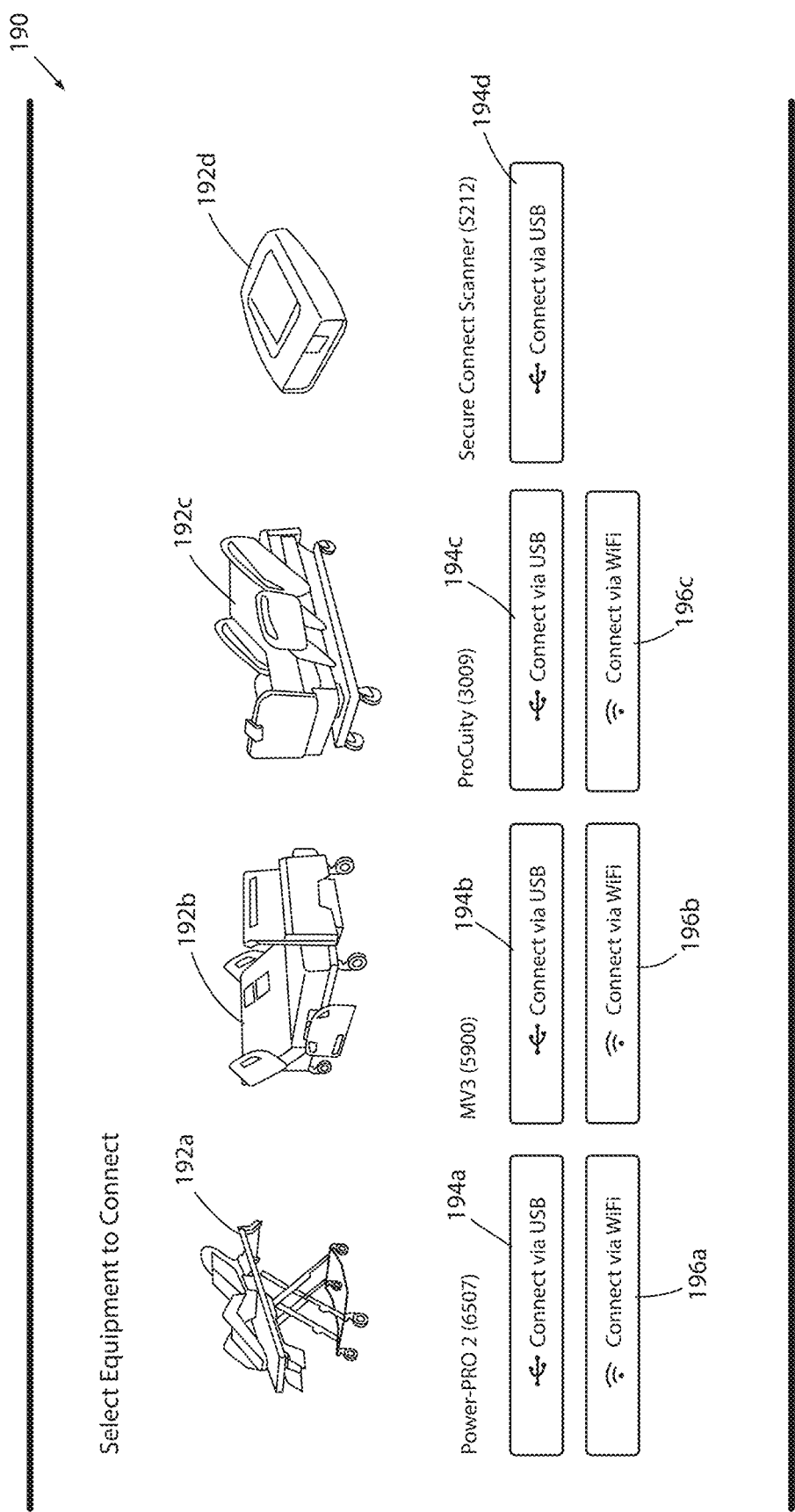
FIG. 7 is an example of a home screen displayed on an embodiment of the service tool.
Figure 8:
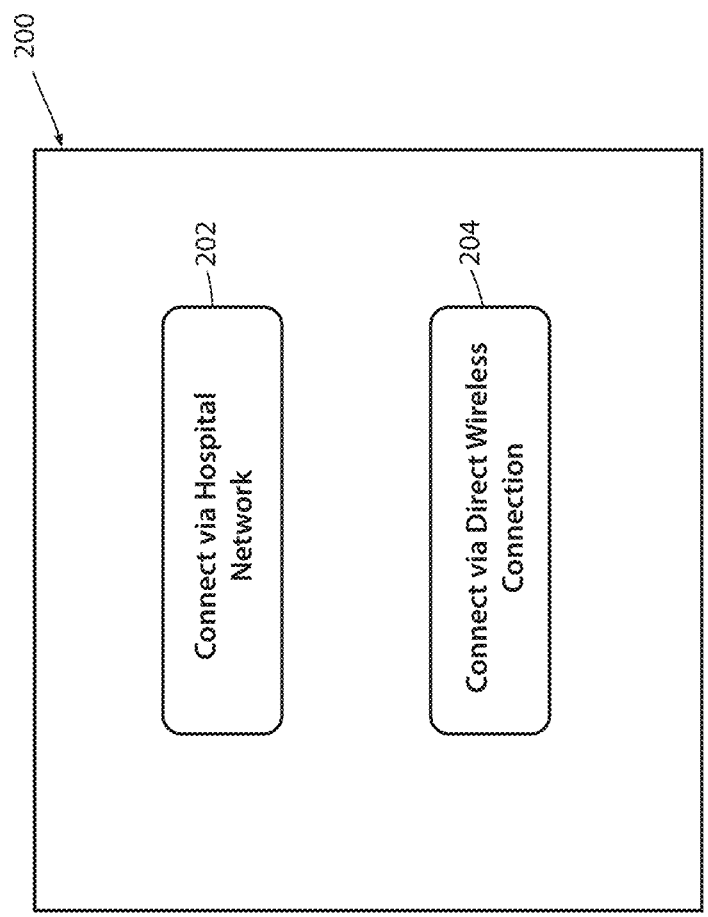
FIG. 8 is an example of a wireless selection screen displayed on an embodiment of the service tool in response to a user selecting the "connect via WiFi" option from the screen of FIG. 7.
Figure 9:
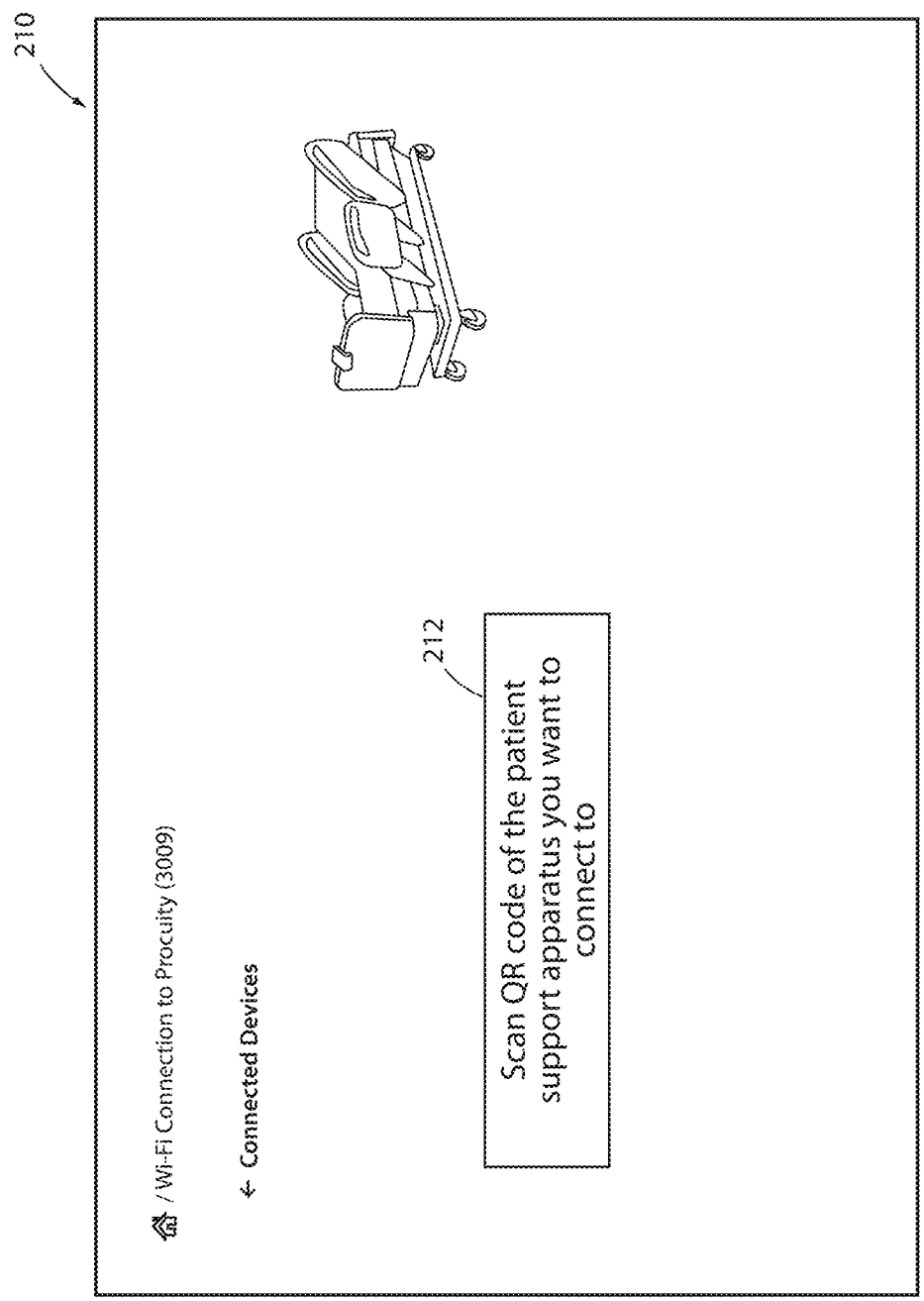
FIG. 9 is an example of a screen displayed on an embodiment of the service tool in response to a user selecting the "connect via direct wireless connection" option from the screen of FIG. 8.
Figure 10:
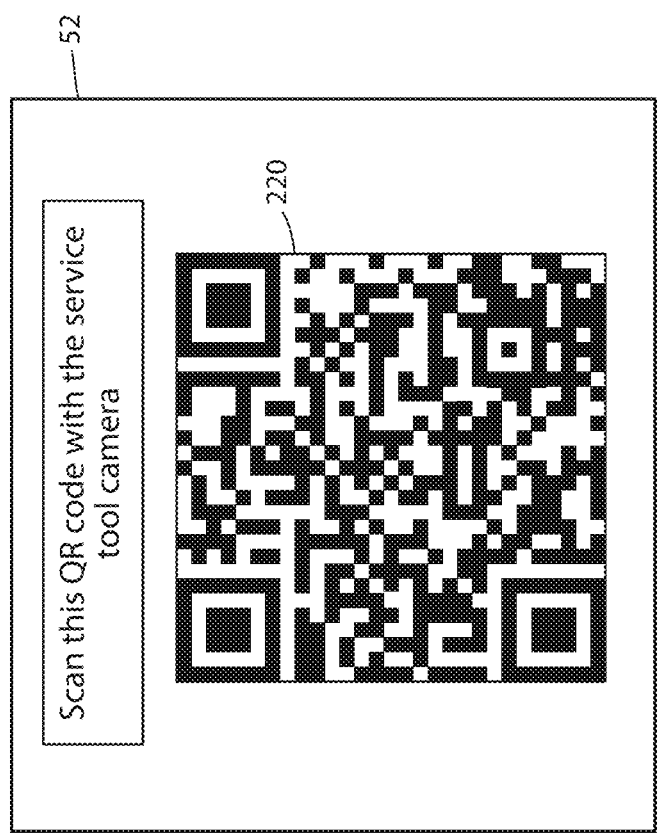
FIG. 10 is an example of a coded image displayed on a screen of some embodiments of the patient support apparatus.

In the third embodiment mentioned above, in which service tool 94 is configured to advertise a wireless network having credentials that are generated by patient support apparatus 20 using network credential generator algorithm 134, the steps carried out by patient support apparatuses 20 and service tool 94 are described in more detail with respect to FIGS. 5-9. Specifically, in this embodiment, FIG. 5 illustrates an algorithm carried out by controller 104 of patient support apparatus 20; FIG. 6 illustrates an algorithm carried out by controller 114 of service tool 94; FIGS. 7-9 illustrate exemplary screens that may be displayed on display of service tool 94 during the performance of these algorithms (and/or other algorithms); and FIG. 10 illustrates an exemplary screen that is displayed on display 52 of patient support apparatus 20 during the performance of the algorithm illustrated in FIG. 5.

FIG. 5 illustrates a patient support apparatus algorithm 140 that is adapted to be executed by patient support apparatuses 20 that implement the third embodiment discussed above (that is, patient support apparatuses 20 that utilize network credential generator algorithm 134 to connect to service tool 94). Algorithm 140 begins at step 142 where it proceeds to monitor a network control at step 144. The network control monitored at step 144 refers to a button, a switch, a control, a touchscreen icon, or other type of control that a user is able to selectively activate when he or she wishes to wirelessly connect service tool 94 to patient support apparatus 20. In some embodiments of patient support apparatus 20, the network control monitored at step 144 is a dedicated, hard-wired control, such as a button or switch, that the user must press in order to begin the process of communicatively coupling service tool 94 to patient support apparatus 20. In other embodiments, the network control monitored at step 144 is an icon, symbol, or other control that is displayed on display 52 and that must be touched in order to activate it. In some of these latter embodiments, the network control may only be visible on display 52 after the user navigates to a particular screen shown thereon, such as a diagnostic, service, settings, or other type of screen.

Regardless of the position, location, and/or type of network control that is implemented on patient support apparatus 20, controller 104 monitors this control at step 144 and proceeds to step 146 where it determines if the network control was activated or not. If it was not, it returns to step 144 and continues to monitor the network control. If it was, it proceeds to step 148. At step 148, controller 104 uses network credential generator algorithm 134 to generate a random, or pseudo-random, SSID. From step 148, controller 104 proceeds to step 150 where it uses network credential generator algorithm 134 to generate a random, or pseudo-random, password. In some embodiments, controller 104 generates the random or pseudo-random SSID and password at steps 148 and 150 utilizing conventional random or pseudo-random number generators.

As an alternative to generating the actual SSID and/or password, controller 104 may generate at steps 148 and/or 150 a random number, character string, key, or other data structure that will be processed by service tool 94 into an SSID and/or password. In other words, in some embodiments, instead of generating an actual SSID and/or password, controller 104 may generate one or more inputs that, after being transmitted to service tool 94, are used by controller 114 as inputs into a function that uses them to generate an SSID and/or a password. In such embodiments, controller 104 of patient support apparatus 20 has access to the same function used by controller 114 of service tool 94 so that controller 104 can use those same inputs and function to generate the same SSID and/or password. In other words, controller 104 is configured so that it will end up knowing the same SSID and/or password that controller 114 ends up having (either as a result of the SSID and/or password being directly passed from patient support apparatus 20 to service tool 94, or as the result of one or more inputs being passed from patient support apparatus 20 to service tool 94 that are then used to generate an SSID and/or password).

Returning to step 152 of algorithm 140 (FIG. 5), controller 104 proceeds to encode the SSID and password (or inputs to a function) that were generated at steps 148 and 150. In at least one embodiment, this encoding involves generating a conventional Quick Response (QR) code that visually encodes the outputs from step 148 and 150. It will be understood, however, the controller 104 may be programmed to encode the outputs of steps 148 and 150 in codes different from QR codes, such as, but not limited to, bar codes and/or other visual types of codes.

Regardless of the specific code used as step 152, controller 104 then proceeds to step 154 where it displays the code (e.g. the QR code) that was generated at step 152 on the display 52 of patient support apparatus 20. At, or near, the time controller 104 displays the code on display 52, it starts a timer, in at least some embodiments. The timer is set for an amount of time that is reasonable for a person to scan the code (e.g. QR code) displayed on display 52 using service tool 94's camera 122 and then have service tool 94 set up a temporary wireless network using the SSID and password generated at steps 148 and 150 (and for controller 104 and network transceiver 82 to join that network), as will be discussed in greater detail below. In some embodiments, the timer of step 156 therefore may be on the order of one to ten minutes, although it will be understood that other times may of course be used. Further, as noted above, in some embodiments, step 156 may be eliminated entirely and no timer used with algorithm 140.

After completing step 156 (FIG. 5), controller 104 of patient support apparatus 20 proceeds to step 158 where it looks for a wireless network that is advertising the SSID that it generated at step 148 (or that is advertising the SSID that was generated from a function utilizing the input generated at step 148). Controller 104 thus uses network transceiver 82 to "listen" for a wireless network with the SSID that resulted from step 148. Once it detects this network, it attempts to connect to it using the password that was generated at step 150 (either directly, or as an input into a password generating function). At step 160, it determines whether it is able to successfully connect to the network with the SSID and password of steps 148 and 150. If it is not, it proceeds to step 162. If it is, it proceeds to join the wireless network with that SSID and password using network transceiver 162. At step 162, controller 162 checks to see if the timer started at step 156 has expired. If it has, it returns to step 144 and proceeds in the manner previously recited. If it has not, it returns to step 158 and continues looking for the network with the SSID and password of steps 148 and 150.

It can thus be seen that the effect of the timer of steps 156 and 162 is to limit the time window during which a user can connect patient support apparatus 20 to a wireless network having the SSID and password of steps 148 and 150. This timer window helps reduce the potential for unauthorized access being gained to patient support apparatus 20 by limiting the times at which patient support apparatus 20 will automatically connect to a wireless network. Further, by setting the timer long enough to allow a technician to have patient support apparatus 20 automatically connect to the wireless network of service tool 94, the timer does not inhibit the authorized functions carried out by the technician who is using service tool 94.

Once controller 104 and network transceiver 82 have joined the wireless network at step 164, controller 104 is configured to receive one or more software updates from service tool 94 via the wireless network, report diagnostic data and/or other data to service tool 94 using the wireless network, and/or carry out any other desired communications between patient support apparatus 20 and service tool 94. After service tool 94 is moved out of range of network transceiver 82 and/or service tool 94 shuts down the wireless network (which is only used for temporary access to the patient support apparatus 20), controller 104 and network transceiver 82 of patient support apparatus 20 disconnect from the wireless network and return to step 144 of algorithm 140. When proceeding through algorithm 140 a second, or subsequent time, it bears noting that the SSID and password generated at steps 148 and 150 will be different from the SSID and password previously generated at these steps during a previous iteration of algorithm 140. However, is some modified embodiments, algorithm 140 could be modified to only generate a different password at each iteration of algorithm 140 but still continue to use the same SSID, or vice versa. Still other modifications of algorithm 140 are possible.

In the foregoing embodiment, patient support apparatus 20 and/or service tool 94 may be configured to only couple together directly over the temporary wireless network a single time. In such embodiments, if the temporary wireless connection is prematurely lost, the devices will not be able to re-establish communication with each other over the same wireless network. Instead, patient support apparatus 20 will generate a new set of credentials using algorithm 134, display a new code (e.g. a QR code), and the user of service tool 94 will have to scan that new code using camera 122 in order to re-establish communication with patient support apparatus 20. Thus, it can be seen that if communication fails over the temporary wireless network, a new temporary wireless network having new credentials will need to be implemented in order to re-establish communication, in at least some embodiments. In still other embodiments, attempts to re-establish communication over the same temporary wireless network may be automatically made for a set period of time before requiring that a new wireless network with new credentials be used. Still other variations are possible.

FIG. 6 illustrates a service tool algorithm 170 that is implemented by controller 114 of service tool 94 when controller 114 executes service tool application 136. Service tool algorithm 170 is followed by service tool 94 when controller 104 of patient support apparatus 20 executes algorithm 140 (FIG. 5). In other words, algorithms 140 and 170 are used together, the former being implemented by patient support apparatus 20 and the latter being implemented by service tool 94.

Service tool algorithm 170 begins at a start step 172. Start step 172 may be accomplished by a user tapping, or double tapping, on an icon on the display of 120 of service tool 94 that corresponds to service tool application 136, or by any other conventional means of starting a software application on an electronic device such as a smart phone, table computer, laptop computer, or other type of computer. Once started, algorithm 170 proceeds to step 172 where it utilizes camera 122 to capture an image of the code (e.g. QR code) displayed on display 52 of patient support apparatus 20 as part of step 154 of algorithm 140. Step 174, in some embodiments, includes displaying one or more instructions on display 120 that instruct the user of service tool 94 to take a picture of the QR code (or other type of code) displayed on patient support apparatus 20 using camera 122 (see, e.g. the instructions of FIG. 9). Once camera 122 has captured the QR code (or other type of code) at step 174, controller 114 proceeds to step 176 where it decodes the QR code (or other type of code). As was mentioned previously, the QR code may directly identify an SSID and/or password, or it may provide inputs into a function that is used to generate an SSID and/or a password. Service tool application 136 is programmed to interpret the decoded data from the QR code at step 176 either as an SSID and password, or as inputs into a function it then uses to generate an SSID and password. In either case, after decoding the data contained within the image captured at step 174, controller 114 moves to step 178 where it creates a wireless network bearing the SSID and password that it determined at step 176. This creation of a wireless network may be carried out in conventional manners, such as by creating and/or advertising a WiFi hotspot or other wireless WiFi network access point. Thus, at step 178, controller 114 instructs wireless network transceiver 118 to transmit one or more signals advertising the existence of a wireless network with the SSID determined from step 176.

From step 178, controller 114 proceeds to step 180 where it waits to receive signals (via network transceiver 118) indicative of a device attempting to join this wireless network. If a device attempts to join, controller 114 proceeds to step 182 and checks to see if the device that is attempting to join has forwarded the correct password or not. If the device does not have the correct password, it is not allowed to join the network. If it does have the correct password, it is allowed to join the network at step 184.

Because the SSID and password for the network were transmitted to service tool 94 from patient support apparatus 20 via the QR code, the only device that should have the proper credentials (SSID and password) to join the wireless network created by service tool 94 at step 178 is the patient support apparatus 20. Accordingly, only the patient support apparatus 20 that displayed the code captured at step 174 will be able to join the network of service tool 94. This ensures that the user of service tool 94 will only be connected to the particular patient support apparatus 20 that displayed the QR code that he or she scanned (captured the image of) with service tool 94. The user of service tool therefore doesn't need to take any additional steps, other than activating the network control (step 146 of algorithm 140) on the patient support apparatus 20 he or she wishes to communicate with and capturing the image displayed on the display of that patient support apparatus 20, in order to connect service tool 94 to that particular patient support apparatus 20. As noted, once connected, service tool 94 may thereafter be used to transfer software updates to that patient support apparatus 20, to read diagnostic information from patient support apparatus 20, and/or to carry out other tasks.

FIG. 7 illustrates a home screen 190 that, in some embodiments, service tool application 136 instructs controller 114 to display on display 120 of service tool 94 when application 136 is initially started (as well as at other times). Home screen 190 includes four device images 192*a*-*d* that correspond to four different types of devices that service tool 94 may be configured to connect to. Images 192*a*-*c* correspond to different types of patient support apparatuses, while image 192*d* corresponds to a headwall configuration tool. Of the patient support apparatuses 20, image 192*a* corresponds to a cot; image 192*b* corresponds to a first type of hospital bed; and image 192*c* corresponds to a second type of hospital bed.

For each image 192*a*, home screen 190 provides one or more connection options, such as wired connections options 194*a*-*d* and wireless connection options 196*a*-*c*. The user of service tool 94 selects which image 192*a*-*d* corresponds to the type of device he or she wishes to connect to, and then selects one of the connection options 194 or 196. If the user selects one of the wired connection options 194*a*-*d*, the user couples a conventional USB cable between the USB port of the device (e.g. port 110 of patient support apparatus 20) and the USB port of 124 of service tool 94. Service tool 94 is then able to carry out the software update, diagnostic, and other functions discussed herein with respect to the connected device. When the user selects any of these wired connections, patient support apparatus 20 and service tool 94 do not utilize either of algorithms 140, 170, but instead establish their communication session via the connected USB cable.

If the user selects any of the wireless options 196*a*-*c*, service tool 94 is configured, in at least some embodiments, to display a screen, such as screen 200 of FIG. 8, which will be discussed in greater detail below. Before turning to screen 200 of FIG. 8, however, it should be pointed out that the device 192*d* shown in FIG. 7 is a tool useful for configuring headwall units 58. In some embodiments, device 192*d* is the same as, and includes the same functions and features as, the portable configuration tool 400 disclosed in commonly assigned U.S. patent application Ser. No. 63/131,508 filed Dec. 29, 2020, by inventors Kirby Neihouser et al. and entitled TOOL FOR CONFIGURING HEADWALL UNITS USED FOR PATIENT SUPPORT APPARATUS COMMUNICATION, the complete disclosure of which is incorporated herein by reference. In other embodiments, service tool 94 may be configured to only connect to patient support apparatuses, in which case home screen 190 may be modified to omit tool 192*d*. In still other embodiments, service tool 94 may be modified to communicate with still other types of devices beyond those shown in FIG. 7, such as, but not limited to, one or more other types of patient support apparatuses, other medical devices, and/or one or more thermal control units. Such thermal control units include, but are not limited to, the types of thermal control units disclosed in (and modified to include wireless communication abilities) commonly assigned U.S. Pat. No. 10,390,992 issued Aug. 27, 2019, to inventors Christopher Hopper et al. and entitled THERMAL CONTROL SYSTEM, the complete disclosure of which is incorporated herein by reference.

As was noted above, if the user of service tool 94 activates any of the wireless communication options 196*a-c*, service tool application 136 is configured, in at least some embodiments, to instruct controller 114 to display a selection screen, such as the selection screen 200 shown in FIG. 8, on display 120 of service tool 94. Selection screen 200 includes a healthcare facility network connection option 202 and a direct wireless connection option 204. The user selects the healthcare facility network connection option 202 if he or she wishes to connect to one or more patient support apparatuses 20 using the healthcare facility network 80 (i.e. in the manner illustrated in FIG. 11). The user selects the direct connection option 204 if he or she wishes to connect to one or more patient support apparatuses 20 without using the healthcare facility network 80, but instead using a direction connection between service tool 94 and the patient support apparatus (i.e. in the manner illustrated in FIG. 4). After the user makes a selection from screen 200, controller 114 proceeds to a different screen that facilitates the process of connecting service tool 94 to one or more patient support apparatuses 20.

For example, if the user selects the direct wireless connection option 204 of FIG. 8, service tool application 136 is configured, in some embodiments, to instruct controller 114 to display a screen such as screen 210 of FIG. 9, on display 120 of service tool 94. Screen 210 includes a message 212 that instructs the user of service tool 94 to capture the QR code, or other code, that is displayed on the display 52 of patient support apparatus 20 as part of step 154 of algorithm 140 (FIG. 5). Thus, screen 210 may be displayed as part of step 174 of algorithm 170 in order to better explain to the user what action to take using service tool 94.

FIG. 10 illustrates one example of a QR code 220 that may be displayed on display 52 of patient support apparatus 20 in response to the user pressing, or otherwise activating, the network control monitored at step 144 of algorithm 140. In other words, controller 104 may be configured to display a QR code of the type shown in FIG. 10 at step 154 of algorithm 140. As explained herein, after displaying this QR code, the user of service tool 94 captures this image using camera 122 and the controller 114 decodes it to determine what wireless network to set up for communicating with patient support apparatus 20.

If the user of service tool 94 selects the connection via the healthcare facility network option 202 shown in FIG. 8, then, as mentioned above, service tool 94 will connect to one or more patient support apparatuses 20 in the manner shown in FIG. 11. When connecting in this manner, service tool 94 does not set up its own wireless network, but instead uses the existing healthcare facility network 80 to connect to one or more patient support apparatuses 20. In this embodiment, the user must input, or otherwise share with, service tool 94 the SSID and, if applicable, password necessary for service tool 94 to connect to network 80. Once these credentials are input or shared with service tool 94, service tool 94 connects to the healthcare facility network 80 in a conventional manner.

Once service tool 94 is connected to healthcare facility network 80, it uses conventional network discovery tools to determine which patient support apparatuses 20 are also connected to healthcare facility network 80. In at least one embodiment, service tool application 136 instructs controller 114 to display on display 120 of service tool 94 a list of patient support apparatuses 20 that are connected to network 80. One example of this type of list is shown in a listing screen 230 of FIG. 11. As can be seen therein, listing screen 230 includes a table 232 having a plurality of columns 234. First column 234*a* is a selection column that allows the user to select and/or de-select the corresponding patient support apparatuses 20 identified in each row for having their software updated. Second column 234*b* identifies the serial number of each patient support apparatus 20 that is coupled to network 80 (and service tool 94 via network 80). Third column 234*cd* identifies the location of each patient support apparatus 20. This location information, in at least some embodiments, is determined from each patient support apparatus 20 receiving a unique identifier from its adjacent headwall unit 58, wherein those unique identifiers are mapped to specific locations within the healthcare facility during the installation of headwall units 58. And fourth column 234*d* identifies the version of software that is present on each patient support apparatus 20 in table 232.

If the user of service tool 94 wishes to update the software onboard any of the patient support apparatuses 20 shown in column 234*b* of table 232, he or she simply checks the boxes adjacent to those serial numbers in column 234*a*. After checking the desired boxes, the user then presses on the perform update button 236. In response thereto, service tool application 136 instructs controller 114 to forward the selected software update to each of the selected patient support apparatuses 20 via network transceiver 118. As noted, these software updates are communicated over network 80.

Figure 12:
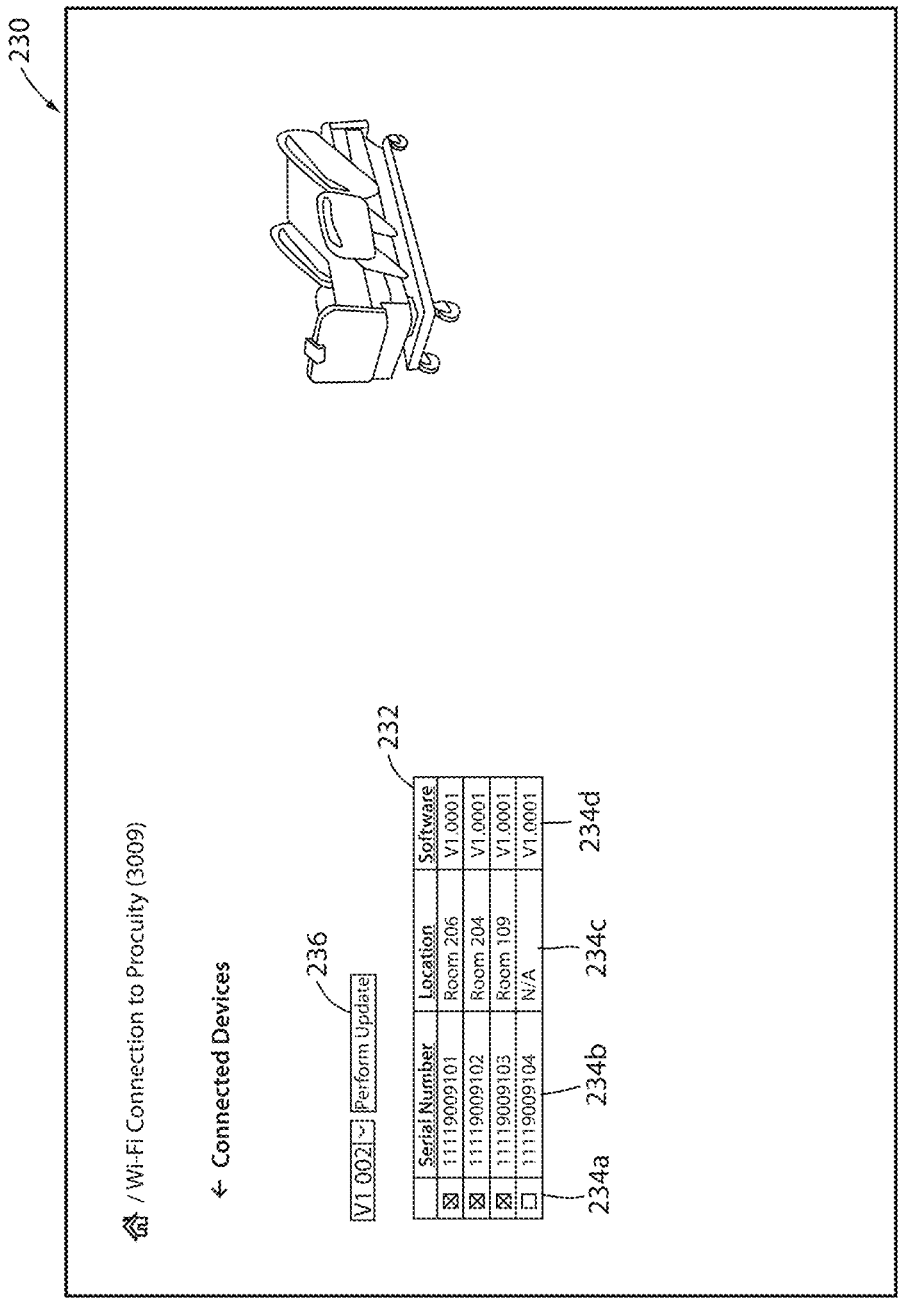
FIG. 12 is an example of a screen displayed on an embodiment of the service tool after the service tool has connected to a plurality of patient support apparatuses on the hospital network.

It will be understood that, although FIG. 12 has been described herein primarily as being displayed on display 120 of service tool 94 in response to the service tool connecting to one or more patient support apparatuses 20 over network 80 (as shown in FIG. 11), service tool application 136 may be configured to instruct controller 114 to display listing screen 230 in response to service tool 94 connecting to one or more patient support apparatuses directly, such as shown in FIG. 4. That is, in those embodiments of patient support apparatus 20 that do not utilize network credential generator algorithm 134, service tool 94 is configured to create a wireless network having credentials that match one of the predefined sets of credentials 130, 132 that are stored in memory 106 onboard patient support apparatuses 20. In such embodiments, when service tool 94 creates this wireless network, any patient support apparatuses 20 that are currently within range of service tool 94 (i.e. within range of network transceiver 118) will join the network created by service tool 94. In many cases, this will result in multiple patient support apparatuses 20 joining the wireless network, in which case controller 114 will display listing screen 230. Thus, it can be seen that service tool application 136 can be configured to instruct controller 114 to display listing screen 230 in any situation where multiple patient support apparatuses 20 are connected to the wireless network created by service tool 94. Further, it can be seen that network credential generator algorithm 134 is used primarily in situations where only a single patient support apparatus 20 connects to service tool 94 at a time. Finally, it should be apparent to those skilled in that art that, when service tool 94 connects to one or more patient support apparatuses 20 via network 80, network transceiver 118 does not need to be within range of the patient support apparatuses 20, but instead only needs to be within range of at least one wireless access point 96 of network 80, and it is then able to communicate with any and all of the patient support apparatuses 20 that are coupled to network 80.

It will be understood by those skilled in the art that various modifications may be made to any of the screens shown herein, as well as to any of the algorithms described herein (including not only algorithms 140 and 170, but also network credential generator algorithm 134). Still further, modifications may also be made to patient support apparatuses 20 and service tool 94 beyond those that have been explicitly discussed herein. As one non-limiting example, service tool 94 may be utilized to set up a wireless network using credentials (SSID/password) that are—instead of being encoded on a display of the patient support apparatus 20—manually entered by the user of service tool 94 into service tool 94 (e.g. via controls 126, which may include an actual and/or virtual keyboard). Thus, for example, if a user wishes to connect directly (e.g. via the method shown in FIG. 4) with a patient support apparatus 20, he or she may read one or more credentials and/or other identifying information from patient support apparatus 20 and then manually type that information into service tool 94. Such information may include the serial number, an SSID and password, and/or other information of patient support apparatus 20. The serial number (or other information) may be displayed on display 52 of patient support apparatus 20 after the user navigates to a certain screen and/or the serial number (or other information) may be displayed on a sticker or other indicia physically attached to the patient support apparatus 20. Once the serial number (or other information) is input into service tool 94, service tool 94 creates a wireless network using that serial number (or other information) as an input for the network credentials, and it does so in a manner that patient support apparatus 20 is programmed to know so that patient support apparatus 20 will thereafter automatically connect to that network.

Thus, in some embodiments, instead of displaying a coded image on display 52 at step 154 of algorithm 140, algorithm 140 may be modified to display an image that is not QR-encoded (or bar-coded or otherwise encoded). In such embodiments, the serial number, SSID, and/or password may be displayed in human-readable form on display 52. Alternatively, the serial number, SSID, and/or password may be displayed in human-readable form (e.g. numbers, letters, etc.), but the human-readable characters may encode the serial number, SSID, and/or password, in which case service tool 94 is programmed to decipher the coded information in the same manner as patient support apparatus 20 so that patient support apparatus 20 will know to connect to the network created by service tool 94 after the user has entered the human-readable characters displayed on display 52. Still other variations are possible.

In another modified embodiment, controller 104 of patient support apparatus 20 is modified to automatically switch its connection to healthcare facility network 80 to the wireless network advertised by service tool 94 when it detects the presence of this network. Further, in this embodiment, controller 104 is further configured to automatically switch back to the hospital area network 80 after the connection between service tool 94 and patient support apparatus 20 is terminated. Thus, for example, if patient support apparatus 20 is currently connected to network 80 and a technician brings a service tool 94 within range of that patient support apparatus 20, controller 104 automatically and temporarily disconnects from network 80 when service tool 94 begins advertising its ad hoc network. After disconnecting, controller 104 joins the ad hoc network advertised by tool 94, performs communications with service tool 94 via the ad hoc network (as directed by the service technician), and then, when those communications are done, it automatically switches back to network 80 after disconnecting from the network advertised by service tool 94. In this manner, the user of service tool 94 has the option of connecting to a patient support apparatus 20 directly via its own network, or through network 80, regardless of whether or not patient support apparatus 20 is connected to network 80 or not. This gives the user of tool 94 more options, particularly in those embodiments of patient support apparatus 20 that are only able to connect to a single wireless network 80 at a time. This feature of automatic and temporary disconnection from network 80 to join the wireless network of tool 94, as well as the automatic reconnection to network 80 after disconnecting from tool 94, may be implemented in any of the embodiments of patient support apparatuses 20 and/or tools 94 discussed above, regardless of whether or not patient support apparatus 20 displays an encoded image, a non-encoded image, coded or non-coded characters, and/or does not display anything related to tool 94 on its display 52.

In some embodiments, service tool 94 may be modified to either omit camera 122 and/or to not utilize camera 122. That is, in those embodiments where service tool 94 only connects to patient support apparatuses 20 via network 80, camera 122 may be omitted or not utilized. Further, in those embodiments of service tool 94 that are able to connect to a patient support apparatus 20 either by network 80 or the ad hoc network created by service tool 94, camera 122 may be omitted or not used these embodiments as well. In such non-camera embodiments, the user may manually enter the network credentials into service tool 94 that service tool then uses to advertise the network to which patient support apparatus 20 is to join. Alternatively, or additionally, patient support apparatuses 20 may be programmed, such as during their manufacturing process, to automatically connect to a particular network name (using a particular password), and this network and password may be stored in memory 116 of service tool 94 (and utilized by service tool application 136), thereby avoiding the need for any network credentials to be transmitted from patient support apparatus 20 to service tool 94. Still other non-camera embodiments are possible.

It will also be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
   a support surface adapted to support a person;
   a wireless network transceiver;
   a memory containing a first network identifier and a second network identifier, the first network identifier different from the second network identifier;
   a display;
   a control; and
   a controller in communication with the memory, the display, the control, and the wireless network transceiver, the controller adapted to display a coded image on the display in response to activation of the control, to use the wireless network transceiver to automatically connect to, and to send a first password to, a first wireless network bearing the first network identifier, and to automatically connect to, and send a second password to, a second wireless network bearing the second network identifier, wherein the first wireless network is advertised by a wireless access point of a healthcare facility and the second wireless network is advertised by a hand-held service tool, and wherein the coded image encodes the second network identifier, the controller still further adapted to display a different coded image in response to a subsequent activation of the control, wherein the different coded image encodes a different network identifier and wherein the controller is further adapted to use the wireless network transceiver to automatically connect to a different wireless network bearing the different network identifier.

2. The patient support apparatus of claim 1 wherein the controller is further adapted to simultaneously connect to both the first wireless network and the second wireless network.

3. The patient support apparatus of claim 2 wherein the controller is further configured to receive a software update from both the first wireless network and the second wireless network.

4. The patient support apparatus of claim 1 wherein the coded image includes a Quick Response (QR) code, the wireless network transceiver is a WiFi transceiver, the first network identifier includes a first Service Set Identifier (SSID), and the second network identifier includes a second SSID.

5. The patient support apparatus of claim 1 wherein the controller is configured to automatically connect to the second wireless network only for a fixed amount of time after displaying the coded image on the display, and to not connect to the second wireless network after the fixed amount of time expires.

6. The patient support apparatus of claim 1 wherein the controller is configured to only connect to the second wireless network a single time such that, if the controller becomes disconnected from the second wireless network, the controller is adapted to not automatically re-connect to the second wireless network.

7. The patient support apparatus of claim 1 wherein the coded image further encodes the second password for the second wireless network.

8. The patient support apparatus of claim 1 further comprising a Universal Serial Bus (USB) port adapted to receive a software update from a service tool coupled to the USB port via a USB cable.

* * * * *